United States Patent [19]
Slassi et al.

[11] Patent Number: 5,998,438
[45] Date of Patent: Dec. 7, 1999

[54] 5-CYCLO INDOLE COMPOUNDS

[75] Inventors: Abdelmalik Slassi; Louise Edwards, both of Mississauga; Qingchang Meng, Georgetown; Sumanas Rakhit, Mississauga, all of Canada

[73] Assignee: Allelix Biopharmaceuticals, Inc., Ontario, Canada

[21] Appl. No.: 08/976,103

[22] Filed: Nov. 21, 1997

Related U.S. Application Data

[60] Provisional application No. 60/069,887, Nov. 26, 1996.

[51] Int. Cl.$^6$ ...................... C07D 209/14; C07D 401/04; A61K 31/40
[52] U.S. Cl. .......................... 514/316; 514/318; 514/323; 514/333; 514/339; 514/414; 514/415; 546/187; 546/193; 546/201; 546/256; 546/277.4; 548/466; 548/504; 424/1.65
[58] Field of Search ...................................... 514/316, 318, 514/323, 333, 339, 414, 415; 546/187, 193, 201, 256, 277.4; 548/466, 504

[56] References Cited

U.S. PATENT DOCUMENTS

| 5,298,520 | 3/1994 | Baker et al. | 514/383 |
| 5,300,645 | 4/1994 | Audia et al. | 546/49 |
| 5,502,065 | 3/1996 | Brown et al. | 514/339 |
| 5,508,284 | 4/1996 | Audia et al. | 514/285 |
| 5,510,359 | 4/1996 | Pineiro et al. | 514/361 |

FOREIGN PATENT DOCUMENTS

| 0 225 726 | 6/1987 | European Pat. Off. |
| 0 313 397 | 4/1989 | European Pat. Off. |
| 0 438 230 | 7/1991 | European Pat. Off. |
| 0 497 512 | 8/1992 | European Pat. Off. |
| 0 581 538 | 2/1994 | European Pat. Off. |

OTHER PUBLICATIONS

Castro et al., J. Med. Chem. 1994, 37, 3023–3032, "Synthesis and Biological Activity of 3–[2 –(Dimethylamino)ethyl]–5–[1,1–dioxo–5–methyl–1,2, 5–thiadiazolidin–2–yl)–methyl]–1H–indole . . .".
International Application No. WO 94/14771 published Jul. 7, 1994.
International Publication No. WO 93/20073 published Oct. 14, 1993.
International Publication No. WO 92/13856 published Aug. 20, 1992.
International Publication No. WO 95/32196 published Nov. 30, 1995.
International Publication No. WO 94/02476 published Feb. 3, 1994.
International Publication No. WO 95/21167 published Aug. 10, 1995.

(List continued on next page.)

*Primary Examiner*—Mukund J. Shah
*Assistant Examiner*—Deepak R. Rao
*Attorney, Agent, or Firm*—Nikaido Marmelstein Murray & Oram, LLP

[57] ABSTRACT

Described herein are compounds selective for a 5-HT$_{1D}$-like receptor, which have the general formula:

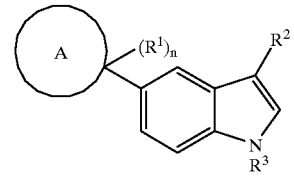

wherein A is selected from a six-membered, non-aromatic, optionally substituted carbocycle and a six-membered, non-aromatic, optionally substituted heterocycle having one or two heteroatoms selected from O, S, SO, SO$_2$ and N$^4$;

R$^1$ is selected from H and OH;

n is 0 or 1 as permited by chemical structure;

R$^2$ is selected from CR$^5$CR$^6$CH$_2$NR$^7$R$^8$ or a group of formula II, III or IV:

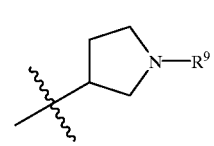

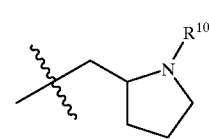

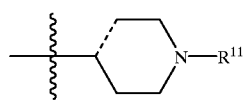

R$^3$ is selected from H and benzoyl;

R$^4$ is selected from H, loweralkyl, benzyl, loweralkylcarbonyl, loweralkylaminocarbonyl, loweralkylaminothiocarbonyl, loweralkanoyl, loweralkylaminoimide and loweralkoxy-substituted loweralkylene;

R$^5$ and R$^6$ are independently selected from H, loweralkoxy and hydroxy;

R$^7$ and R$^8$ are independently selected from H and loweralkyl or R$^7$ and R$^8$ form an alkylene bridge which, together with the nitrogen atom to which they are attached, creates an optionally substituted 3- to 6-membered ring;

denotes a single or double bond; and

R$^9$, R$^{10}$ and R$^{11}$ are independently selected from H and loweralkyl.

Also described is the use of these compounds as pharmaceuticals to treat indications where stimulation of a 5-HT$_{1D}$-like receptor is implicated, such as migraine.

40 Claims, No Drawings

OTHER PUBLICATIONS

International Publication No. WO 95/06636 published Mar. 9, 1995.

Street et al., *J. Med. Chem.* 1993, 36, pp. 1529–1538, "Synthesis and Serotonergic Activity of 5–(Oxadiazolyl) tryptamines: Potent Agonists for 5–$HG_{ID}$ Receptors".

International Publication No. WO WO 94/08993 published Apr. 28, 1994.

International Publication No. WO 95/28400 published Oct. 26, 1995.

International Publication No. WO 94/24127 published Oct. 27, 1994.

5-CYCLO INDOLE COMPOUNDS

This application claims the benefit of U.S. Provisional Application No. 60/069,887, filed Nov. 26, 1996.

This invention relates to carbo- and heterocyclic-substituted indole compounds, to pharmaceutical compositions containing them and to their medical use, particularly in the treatment of CNS conditions.

According to one aspect of the invention, there are provided compounds of Formula I and a stereoisomer, solvate, hydrate or pharmaceutically acceptable salt thereof:

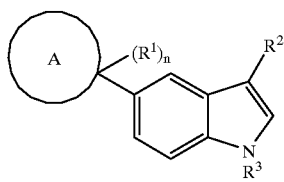

I wherein A is selected from a six-membered, non-aromatic, optionally substituted carbocycle and a six-membered, non-aromatic, optionally substituted heterocycle having one or two heteroatoms selected from O, S, SO, $SO_2$ and $NR^4$;

$R^1$ is selected from H and OH;

n is 0 or 1 as permitted by chemical structure;

$R^2$ is selected from $CR^5R^6CH_2NR^7R^8$ or a group of formula II, III or IV:

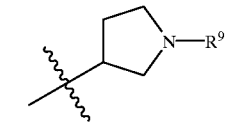

II

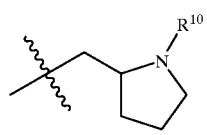

III

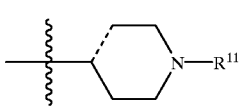

IV $R^3$ is selected from H and benzoyl;

$R^4$ is selected from H, loweralkyl, benzyl, loweralkylcarbonyl, loweralkylaminocarbonyl, loweralkylaminothiocarbonyl, loweralkanoyl, loweralkylaminoimide and loweralkoxy-substituted loweralkylene;

$R^5$ and $R^6$ are independently selected from H, loweralkoxy and hydroxy;

$R^7$ and $R^8$ are independently selected from H and loweralkyl or $R^7$ and $R^8$ form an alkylene bridge which, together with the nitrogen atom to which they are attached, creates an optionally substituted 3- to 6-membered ring;

denotes a single or double bond; and $R^9$, $R^{10}$ and $R^{11}$ are independently selected from H and loweralkyl; with the proviso that when A is cyclohexane and $R^3$ is H, then $R^2$ is not $CH_2CH_2NH_2$.

According to another aspect of the invention, there is provided a pharmaceutical composition comprising a compound of Formula V in an amount effective to stimulate 5-HT$_{1D}$-like receptors, and a pharmaceutically acceptable carrier:

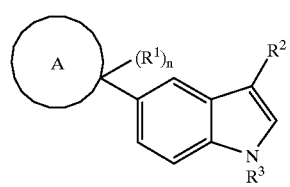

V wherein A is selected from a six-membered, non-aromatic, optionally substituted carbocycle and a six-membered, non-aromatic, optionally substituted heterocycle having one or two heteroatoms selected from O, S, SO, $SO_2$ and $NR^4$;

$R^1$ is selected from H and OH;

n is 0 or 1 as permitted by chemical structure;

$R^2$ is selected from $CR^5R^6CH_2NR^7R^8$ or a group of formula II, III or IV:

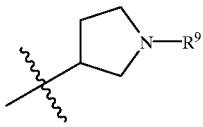

II

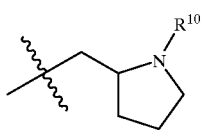

III

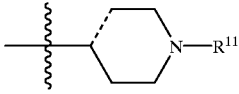

IV $R^3$ is selected from H and benzoyl;

$R^4$ is selected from H, loweralkyl, benzyl, loweralkylcarbonyl, loweralkylaminocarbonyl, loweralkylaminothiocarbonyl, loweralkanoyl, loweralkylaminoimide and loweralkoxy-substituted loweralkylene;

$R^5$ and $R^6$ are independently selected from H, loweralkoxy and hydroxy;

$R^7$ and $R^8$ are independently selected from H and loweralkyl or $R^7$ and $R^8$ form an alkylene bridge which, together with the nitrogen atom to which they are attached, creates an optionally substituted 3- to 6-membered ring;

denotes a single or double bond; and $R^9$, $R^{10}$ and $R^{11}$ are independently selected from H and loweralkyl.

In another aspect of the present invention there are provided compositions containing the present compounds in amounts for pharmaceutical use to treat CNS conditions where a 5-HT$_{1D}$-like ligand is indicated and for pharmaceutical use in treating migraine. These and other aspects of the present invention are described in greater detail hereinbelow.

DETAILED DESCRIPTION AND PREFERRED EMBODIMENTS

The term "loweralkyl" as used herein means straight and branched chain alkyl radicals containing from one to six carbon atoms and includes methyl, ethyl, propyl, isopropyl, t-butyl and the like.

The term "six-membered non-aromatic, optionally substituted heterocycle" as used herein means a optionally substituted ring containing zero or one double bonds and one or two heteroatoms selected from O, $NR^4$, S, SO and $SO_2$ (includes dihydropyran, tetrahydropyran, azacyclohexane, azacyclohexene, dihydrothiapyran, tetrahydrothiapyran and the like).

The term "six-membered, optionally substituted non-aromatic carbocycle" as used herein means an optionally substituted carbon ring which optionally contains one double bond and includes cyclohexane and cyclohexene.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formulae I and V or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

"Solvate" means a compound of Formula I or V or the pharmaceutically acceptable salt of a compound of Formula I or V wherein molecules of a suitable solvent are incorporated in a crystal lattice. A suitable solvent is physiologically tolerable at the dosage administered as the solvate. Examples of suitable solvents are ethanol and the like.

The term "stereoisomers" is a general term for all isomers of the individual molecules that differ only in the orientation of their atoms in space. It includes image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Compounds of Formulae I and V include those in which A is selected from a six-membered, non-aromatic, optionally substituted carbocycle and a six-membered, non-aromatic, optionally substituted heterocycle having one or two heteroatoms selected from O, S, SO, $SO_2$ and $NR^4$. When substituted, A can incorporate, at sites appropriate to its chemical structure, one to three substituents, suitably one to two substituents, more suitably one substituent, selected independently from loweralkyl, hydroxy, loweralkoxy and loweralkoxy-substituted loweralkylene. In suitable embodiments, the substituents on A are selected independently from methyl, hydroxy, methoxy and methoxymethylene. It should be noted that the above definition for the substitution of A does not include the groups $R^1$ and $R^4$. These groups have been dealt with separately.

In embodiments of the invention, A is an optionally substituted, six-membered non-aromatic heterocycle having one heteroatom selected from O, S, SO, $SO_2$ and $NR^4$. In preferred embodiments A is an unsubstituted six-membered non-aromatic heterocycle having one heteroatom selected from O, S, SO, $S_2$ and $NR^4$. In more preferred embodiments, A is an unsubstituted heterocycle having one heteroatom selected from O, S, and $NR^4$. In specific embodiments of the invention, A is selected from cyclohexane, cyclohexene, dihydropyran, tetrahydropyran, dihydrothiapyran, tetrahydrothiapyran, azacyclohexane and azacyclohexene. In more specific embodiments, A is selected from azacyclohexan-4-yl, azacyclohex-3-en-4-yl, cyclohex-1-en-1yl, tetrahydrothiapyran4-yl, 3,4-dihydrothiapyran4-yl, 2,3-dihydropyran-2-yl, tetrahydropyran-2-yl, 3,4-dihydropyran4-yl and tetrahydropyran4-yl.

In an embodiment of the invention, n is 0 or 1 and $R^1$ is selected from H and OH. In a preferred embodiment n is 0, i.e. there is a double bond between the carbon to which $R^1$ is attached and the adjacent node. When n is 1, $R^1$ is preferentially H.

In further embodiments of the invention, $R^3$ is selected from H and benzoyl. In a preferred embodiment, $R^3$ is H.

Compounds of Formulae I and V include those in which $R^2$ is selected from $CR^5R^6CH_2NR^7R^8$ or a group of Formula II, III or IV:

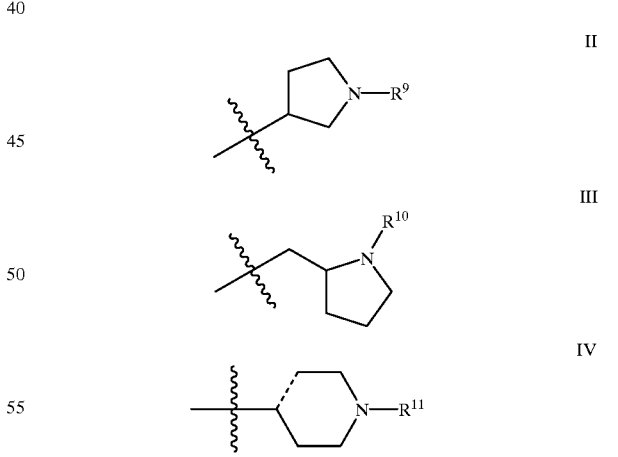

When $R^2$ is $CR^5R^6CH_2NR^7R^8$, $R^5$ and $R^6$ are selected from H, OH and loweralkoxy and $R^7$ and $R^8$ are selected from H and loweralkyl or $R^7$ and $R^8$ form an alkylene bridge which, together with the nitrogen atom to which they are attached, creates a 3- to 6-membered ring optionally substituted with one or two groups selected from loweralkyl, hydroxy and loweralkoxy. Preferably, when one of $R^5$ or $R^6$ is OH or loweralkoxy, the other is H or, more preferably, both $R^5$ and R6 are H. In other preferred embodiments, $R^7$ and $R^8$ are either both methyl or together with the nitrogen atom to which they are attached, form a 3-6-membered, particularly 5-6-membered, unsubstituted saturated ring. Specific rings include pyrrolidine or piperidine. When $R^2$ is a group of Formula II, III or IV, $R^9$, $R^{10}$ and $R^1$ are selected independently from H and loweralkyl, preferably methyl. In more preferred embodiments, $R^5$, $R^6$, $R^7$ and $R^8$ are selected to provide

or $CH_2CH_2NMe_2$.

In embodiments of the invention, $R^4$ is selected from H, loweralkyl, benzyl, loweralkylcarbonyl, loweralkylaminocarbonyl, loweralkylaminothiocarbonyl, loweralkylaminoimide, loweralkoxycarbonyl and loweralkoxy-substituted loweralkylene. In preferred embodiments, $R^4$ is selected from methyl, benzyl and tert-butoxycarbonyl.

In specific embodiments of the invention, the compounds of Formulae I and V include:
5-(Cyclohex-1-en-1-yl)-3-[2-(N,N-dimethylamino)ethyl]-1H-indole;
3-[2-(N,N-Dimethylamino)ethyl]-5-(tetrahydropyran-2-yl)-1H-indole;
(S)-5-(1-Aza-1-tert-butoxycarbonylcyclohex-3-en-4-yl)-3-[(N-methylpyrrolidin-2-yl)methyl]-1H-indole;
5-(1-Aza-1-tert-butoxycarbonylcyclohex-3-en-4-yl)-3-[2-(N,N-dimethylamino)ethyl]-1H-indole
5-(3,4-Dihydropyran-4-yl)-3-[2-(N,N-dimethylamino)ethyl]-1H-indole;
5-(1-Hydroxycyclohex-1-yl)-3-(2-pyrrolidinylethyl)-1H-indole;
5-(1-Aza-1-benzyl-4-hydroxycyclohex-4-yl)-3-(2-pyrrolidinylethyl)-1H-indole;
5-(1-Aza-1-tert-butoxycarbonyl-4-hydroxycyclohex-4-yl)-3-(2-pyrrolidinylethyl)-1H-indole;
5-(1-Aza-1-methyl-4-hydroxycyclohex-4-yl)-3-(2-pyrrolidinylethyl)-1H-indole;
5-(1-Aza-1-methyl-4-hydroxycyclohex-4-yl)-3-[2-(N,N-dimethylamino)ethyl]-1H-indole;
5-(Cyclohex-1-en-1-yl)-3-(2-pyrrolidinylethyl)-1H-indole;
5-(1-Aza-1-benzylcyclohex-3-en-4-yl)-3-(2-pyrrolidinylethyl)-1H-indole;
5-(1-Aza-1-methylcyclohex-3-en-4-yl)-3-(2-pyrrolidinylethyl)-1H-indole;
5-(1-Aza-1-methylcyclohex-3-en-4-yl)-3-[2-(N,N-dimethylamino)ethyl]-1H-indole;
5-Cyclohexyl-3-[2-(N,N-dimethylamino)ethyl]-1H-indole;
5-Cyclohexyl-3-(2-pyrrolidinylethyl)-1H-indole;
5-(1-Aza-1-benzylcyclohex-4-yl)-3-(2-pyrrolidinylethyl)-1H-indole;
(S)-5-(1-Aza-1-tert-butoxycarbonylcyclohex-4-yl)-3-[(N-methylpyrrolidin-2-yl)methyl]-1H-indole
5-(1-Aza-1-tert-butoxycarbonylcyclohex-4-yl)-3-[2-(N,N-dimethylamino)ethyl]-1H-indole;
3-[2-(N,N-Dimethylamino)ethyl]-5-(tetrahydropyran-4-yl)-1H-indole;
5-(1-Azacyclohex-4-yl)-3-(2-pyrrolidinylethyl)-1H-indole;
5-(2,3-Dihydropyran-2-yl)-3-(N-methylpyrrolidin-3-yl)-1-benzoylindole;
5-(2,3-Dihydropyran-2-yl)-3-(2-pyrrolidinylethyl)-1-benzoylindole;
(S)-5-(2,3-Dihydropyran-2-yl)-3-[(N-methylpyrrolidin-2-yl)methyl]-1-benzoylindole;
(R)-5-(2,3-Dihydropyran-2-yl)-3-[(N-methylpyrrolidin-2-yl)methyl]-1-benzoylindole;
5-(2,3-Dihydropyran-2-yl)-3-[2-(N,N-dimethylamino)ethyl]-1-benzoylindole;
3-[2-(-N,N-Dimethylamino)ethyl]-5-(3,4,6-trimethoxyglucal-1-yl)-1-benzoylindole;
3-(2-Pyrrolidinylethyl)-5-(3,4,6-trimethoxyglucal-1-yl)-1-benzoylindole;
5-(2,3-Dihydropyran-2-yl)-3-(N-methylpyrrolidin-3-yl)-1H-indole;
5-(2,3-Dihydropyran-2-yl)-3-[2-(N,N-dimethylamino)ethyl]-1H-indole;
5-(2,3-Dihydropyran-2-yl)-3-(2-pyrrolidinylethyl)-1H-indole;
(S)-5-(2,3-Dihydropyran-2-yl)-3-[(N-methylpyrrolidin-2-yl)methyl]1H-indole;
(R)-5-(2,3-Dihydropyran-2-yl)-3-[(N-methylpyrrolidin-2-yl)methyl]-1H-indole;
3-(2-Pyrrolidinylethyl)-5-(3,4,6-trimethoxyglucal-1-yl)-1H-indole;
3-[2-(N,N-Dimethylamino)ethyl]-5-(3,4,6-timethoxyglucal-1-yl)-1H-indole;
3-(2-Pyrrolidinylethyl)-5-(tetrahydropyran-2-yl)-1H-indole;
5-(2,3-Dihydropyran-2-yl)-3-(2-pyrrolidinylethyl)-1-benzoylindole;
5-(2,3-Dihydropyran-2-yl)-3-[2-(N,N-dimethylamino)ethyl]-1-benzoylindole;
3-[2-(-N,N-Dimethylamino)ethyl]-5-(3,4,6-trimethoxyglucal-1-yl)-1-benzoylindole;
3-(2-Pyrrolidinylethyl)-5-(3,4,6-trimethoxyglucal-1-yl)-1-benzoylindole;
3-[2-(N,N-Dimethylamino)ethyl]-5-(4-hydroxytetrahydropyran-4-yl)-1H-indole;
5-(4-Hydroxytetrahydropyran-4-yl)-3-(2-pyrrolidinylethyl)-1H-indole;
3-[2-(N,N-Dimethylamino)ethyl]-5-(4-hydroxythiapyran-4-yl)-1H-indole;
5-(4-Hydroxythiapyran-4-yl)-3-(2-pyrrolidinylethyl)-1H-indole;
5-(3,4-Dihydropyran-4-3-(2-pyrrolidinylethyl)-1H-indole;
3-(2-Pyrrolidinylethyl)-5-(3,4-dihydrothiapyran-4-yl)-1H-indole;
3-[2-(N,N-Dimethylamino)ethyl]-5-(3,4-dihydrothiapyran-4-yl-1H-indole;
3-(2-Pyrrolidinylethyl)-5-(tetrahydropyran-4-yl)-1H-indole;
3-[2-(N,N-Dimethylamino)ethyl]-5-(1-thiacyclohex-4-yl)-1H-indole;
3-[2-(N,N-Dimethylamino)ethyl]-5-(4-hydroxytetrahydropyran-4-yl)-1H-indole;
5-(1-Aza-1-methyl-4-hydroxycyclohex-4-yl)-3-(1,2,3,6-tetrahydro-1-methyl-4-pyridinyl)-1H-indole and
5-(1-Aza-1-methylcyclohex-4-yl)-3-[2-(N,N-dimethylamino)ethyl]-1H-indole.

In preferred embodiments of the invention, the compounds of Formulae I and V include:
5-(Cyclohex-1-en-1-yl)-3-[2-(N,N-dimethylamino)ethyl]-1H-indole;
3-[2-(N,N-Dimethylamino)ethyl]-5-(tetrahydropyran-2-yl)-1H-indole;
(S)-5-(1-Aza-1-tert-butoxycarbonylcyclohex-3-en-4-yl)-3-[(N-methylpyrrolidin-2-yl)methyl]-1H-indole;
5-(1-Aza-1-tert-butoxycarbonylcyclohex-3-en-4-yl)-3-[2-(N,N-dimethylamino)ethyl]-1H-indole
5-(3,4-Dihydropyran-4-yl)-3-[2-(N,N-dimethylamino)ethyl]-1H-indole;
5-(1-Hydroxycyclohex-1-yl)-3-(2-pyrrolidinylethyl)-1H-indole;

5-(1-Aza-1-methyl-4-hydroxycyclohex-4-yl)-3-[2-(N,N-dimethylamino)ethyl]-1-H-indole;
5-(Cyclohex-1-en-1-yl)-3-(2-pyrrolidinylethyl)-1H-indole;
5-(1-Aza-1-benzylcyclohex-3-en-4-yl)-3-(2-pyrrolidinylethyl)-1H-indole;
5-(1-Aza-1-methylcyclohex-3-en-4-yl)-3-(2-pyrrolidinylethyl)-1H-indole;
5-(1-Aza-1-methylcyclohex-3-en-4-yl)-3-[2-(N,N-dimethylamino)ethyl]-1H-indole;
5-Cyclohexyl-3-[2-(N,N-dimethylamino)ethyl]-1H-indole;
5-Cyclohexyl-3-(2-pyrrolidinylethyl)-1H-indole;
5-(1-Aza-1-benzylcyclohex-4-yl)-3-(2-pyrrolidinylethyl)-1H-indole;
(S)-5-(1-Aza-1-tert-butoxycarbonylcyclohex-4-yl)-3-[(N-methylpyrrolidin-2-yl)methyl]-1H-indole;
5-(1-Aza-1-tert-butoxycarbonylcyclohex-4-yl)-3-[2-(N,N-dimethylamino)ethyl]-1H-indole;
3-[2-(N,N-Dimethylamino)ethyl]-5-(tetrahydropyran-4-yl)-1H-indole;
5-(1-Azacyclohex-4-yl)-3-(2-pyrrolidinylethyl)-1H-indole;
5-(2,3-Dihydropyran-2-yl)-3-(N-methylpyrrolidin-3-yl)-1H-indole;
5-(2,3-Dihydropyran-2-yl)-3-[2-(N,N-dimethylamino)ethyl]-1H-indole;
5-(2,3-Dihydropyran-2-yl)-3-(2-pyrrolidinylethyl)-1H-indole;
(S)-5-(2,3-Dihydropyran-2-yl)-3-[(N-methylpyrrolidin-2-yl)methyl]-1H-indole;
(R)-5-(2,3-Dihydropyran-2-yl)-3-[(N-methylpyrrolidin-2-yl)methyl]-1H-indole;
3-(2-Pyrrolidinylethyl)-5-(tetrahydropyran-2-yl)-1H-indole;
3-[2-(N,N-Dimethylamino)ethyl]-5-(4-hydroxytetrahydropyran-4-yl)-1H-indole;
5-(4-Hydroxytetrahydropyran-4-yl)-3-(2-pyrrolidinylethyly1)-1H-indole;
3-[2-(N,N-Dimethylamino)ethyl]-5-(4-hydroxythiapyran-4-yl)-1H-indole;
5-(4-Hydroxythiapyran-4-yl)-3-(2-pyrrolidinylethyl)-1H-indole;
5-(3,4-Dihydropyran-4-yl)-3-(2-pyrrolidinylethyl)-1H-indole;
3-(2-Pyrrolidinylethyl)-5-(3,4-dihydrothiapyran-4-yl)-1H-indole;
3-[2-(N,N-Dimethylamino)ethyl]-5-(3,4-dihydrothiapyran-4-yl)-1H-indole;
3-(2-Pyrrolidinylethyl)-5-(tetrahydropyran-4-yl)-1H-indole;
3-[2-(N,N-Dimethylamino)ethyl]-5-(1-thiacyclohex-4-yl)-1H-indole;
3-[2-(N,N-Dimethylamino)ethyl]-5-(4-hydroxytetrahydropyran-4-yl)-1H-indole;
5-(1-Aza-1-methyl-4-hydroxycyclohex-4-yl)-3-(1,2,3,6-tetrahydro-1-methyl-4-pyridinyl)-1H-indole; and
5-(1-Aza-1-methylcyclohex-4-yl)-3-[2-(N,N-dimethylamino)ethyl]-1H-indole.

In more preferred embodiments of the invention, the compounds of Formulae I and V include:
5-(1-Hydroxycyclohex-1-yl)-3-(2-pyrrolidinylethyl)-1H-indole;
5-(1-Aza-1-methyl-4-hydroxycyclohex-4-yl)-3-[2-(N,N-dimethylamino)ethyl]-1H-indole;
5-(1-Aza-1-benzylcyclohex-3-en-4-yl)-3-(2-pyrrolidinylethyl)-1H-indole;
5-(1-Aza-1-methylcyclohex-3-en-4-yl)-3-[2-(N,N-dimethylamino)ethyl]-1H-indole;
5-Cyclohexyl-3-(2-pyrrolidinylethyl)-1H-indole;
5-(1-Aza-1-benzylcyclohex-4-yl)-3-(2-pyrrolidinylethyl)-1H-indole;
5-(1-Aza-1-tert-butoxycarbonylcyclohex-4-yl)-3-[2-(N,N-dimethylamino)ethyl]-1H-indole;
5-(1-Azacyclohex-4-yl)-3-(2-pyrrolidinylethyl)-1H-indole;
5-(2,3-Dihydropyran-2-yl)-3-[2-(N,N-dimethylamino)ethyl]-1H-indole;
5-(2,3-Dihydropyran-2-yl)-3-(2-pyrrolidinylethyl)-1H-indole;
(S)-5-(2,3-Dihydropyran-2-yl)-3-[(N-methylpyrrolidin-2-yl)methyl]-1H-indole;
3-[2-(N,N-Dimethylamino)ethyl]-5-(4-hydroxythiapyran-4-yl)-1H-indole;
5-(4-Hydroxythiapyran-4-yl)-3-(2-pyrrolidinylethyl)-1H-indole;
5-(3,4-Dihydropyran-4-yl)-3-(2-pyrrolidinylethyl)-1H-indole;
3-(2-Pyrrolidinylethyl)-5-(3,4-dihydrothiapyran-4-yl)-1H-indole;
3-[2-(N,N-Dimethylamino)ethyl]-5-(tetrahydropyran-4-yl)-1H-indole;
3-[2-(N,N-Dimethylamino)ethyl]-5-(3,4-dihydrothiapyran-4-yl)-1H-indole;
3-(2-Pyrrolidinylethyl)-5-(tetrahydropyran-4-yl)-1H-indole;
5-(1-Aza-1-methylcyclohex-4-yl)-3-[2-(N,N-dimethylamino)ethyl]-1H-indole; and
3-[2-(N,N-Dimethylamino)ethyl]-5-(4-hydroxytetrahydropyran-4-yl)-1H-indole.

In the most preferred embodiments of the invention, the compounds of Formulae I and V include:
5-(1-Aza-1-methylcyclohex-3-en-4-yl)-3-[2-(N,N-dimethylamino)ethyl]-1H-indole;
5-(4-Hydroxythiapyran-4-yl)-3-(2-pyrrolidinylethyl)-1H-indole;
5-(3,4-Dihydropyran-4-yl)-3-(2-pyrrolidinylethyl)-1H-indole;
3-[2-(N,N-Dimethylamino)ethyl]-5-(tetrahydropyran-4-yl)-1H-indole;
3-[2-(N,N-Dimethylamino)ethyl]-5-(3,4dihydrothiapyran-4-yl)-1H-indole;
3-(2-Pyrrolidinylethyl)-5-(tetrahydropyran-4-yl)-1H-indole; and
5-(1-Aza-1-methylcyclohex-4-yl)-3-[2-(N,N-dimethylamino)ethyl]-1H-indole.

Acid addition salts of the compounds of Formulae I and V are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formulae I and V for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

Some of the compounds of the present invention have chiral centres, e.g. those in which $R^5$ or $R^6$ is hydroxy or loweralkoxy and those in which $R^2$ is a group of Formula II or III. The invention extends to cover all structural and optical isomers of the various compounds, as well as racemic mixtures thereof.

The compounds of the present invention can be prepared by processes analogous to those established in the art. Therefore, in general terms, compounds of Formulae I and V can be prepared, for example, by one of two routes. The first involves coupling of an indole of either Formula A or B, wherein Y is a suitable leaving group such as halo or triflate (preferably bromo), with a vinyl trialkylstannane of, for example, Formula C, wherein $X^1$ and $X^2$ are independently selected from $CH_2$, O, S, SO, $SO_2$ or $NR^4$, under standard palladium-cross coupling conditions as shown below in Scheme 1. In this scheme, $R^2$, $R^4$, $R^7$ and $R^8$ are as defined in Formulae I and V. It will be appreciated that other metal coupling reagents could be used in place of the vinyl stannane, for example, a vinyl boronic acid, chloro zinc and the like. Preferred coupling conditions include refluxing the indole and heterocyclic metal reagent in an inert solvent such as dimethylformamide or toluene in the presence of tetrakis(triphenylphosphine) palladium (O). Reduction of the two carbonyls of reagent A can be conducted before or after coupling using metal hydride reducing agents, for example, lithium aluminum hydride in tetrahydrofuran. If this reduction is carried out with a smaller amount of reducing agent, compounds of Formulae I and V, wherein $R^5$ and $R^6$ are independently hydroxyl, can be isolated. This hydroxy group can then be alkylated using standard conditions (for example alkyl halide and potassium carbonate in acetonitrile) to provide compounds of Formulae I and V wherein $R^5$ or $R^6$ is alkoxy. The benzoyl group of reagent B can be removed under standard deprotection conditions, such as sodium hydroxide in methanol, after coupling.

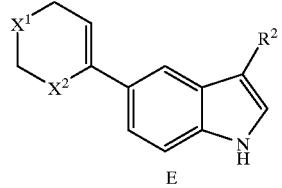

A second route to compounds of Formulae I and V is shown below in Scheme 2. An indole reagent of Formula F, wherein $R^2$ is as defined in Formulae I and V and Y is a suitable leaving group such as halo or triflate (preferably bromo), can be treated with strong base and a ketone of, for example, Formula G (provided the heteroatom is not alpha to the ketone) to provide compounds of Formulae I and V, wherein X is $CH_2$, $NR^4$, S, SO, $SO_2$ or O. This reaction is performed in inert solvents, such as ether or tetrahydrofuran, at temperatures ranging from −78 to 0° C. Preferred conditions are ether at 0° C. for the addition of potassium hydride and −78° C. for the addition of t-butyllithium. Dehydration of these compounds can be performed under standard conditions, for example, formation of the mesylate and elimination under basic conditions or in the presence of an acid such as trifluoroacetic acid in an inert solvent such as tetrahydrofuran, to provide compounds of Formula J.

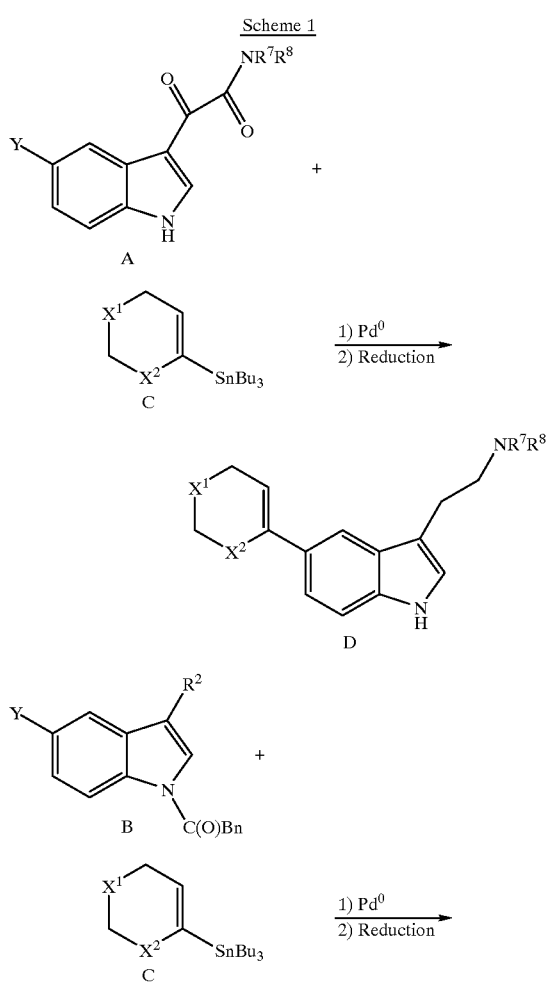

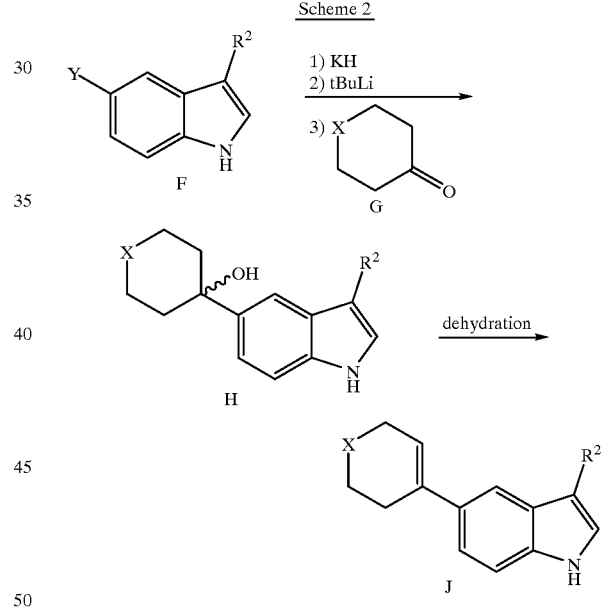

Reduction of the compounds of Formula D, E or J to provide the fully saturated heterocycle can be performed under standard hydrogenation conditions or using metal hydride reducing agents. Preferred hydrogenation conditions are catalytic amounts of palladium on carbon in ethyl acetate in a hydrogen atmosphere at room temperature. Preferred metal hydride reducing agents include lithium aluminum hydride or sodium cyanoborohydride. This reaction can be carried out in ether, tetrahydrofuran or ethanol-acid at temperatures ranging from 0 to 80° C. Preferred conditions are sodium cyanoborohydride in ethanol/HCl at room temperature. It should be noted that when the heteroatom is in the position alpha to the heterocycle's point of attachment to the indole ring in compounds of Formula D or E, metal hydride reduction is preferred over hydrogenation.

Compounds of Formula A, wherein $R^7$ and $R^8$ are as defined in Formulae I and V and Y is as defined above, can be prepared by reaction of indole K with oxalyl chloride followed by reaction with the appropriate amine as shown in Scheme 3. These reactions are conducted in an inert solvent such as diethyl ether (preferred) or dichloromethane, and at temperatures in the range of 0–65° C., preferably 25–65° C.

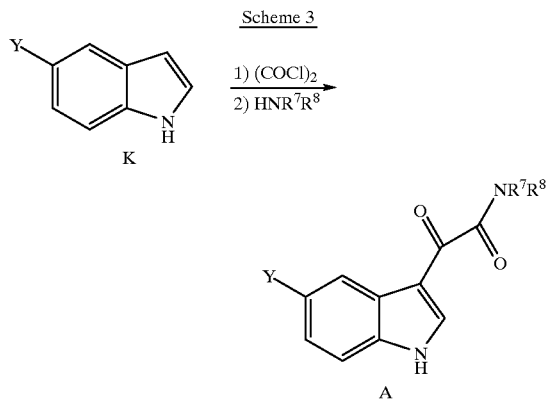

Compounds of Formula B or F wherein $R^2$ is a group of Formula II, can be prepared as shown in Scheme 4. Condensation of indole K, wherein Y is as defined above, with maleimide L ($R^9$ is as defined in Formulae I and V) under acidic conditions at temperatures ranging from about 65–155° C., provides intermediate M. Preferred conditions are acetic acid at temperatures of about 100–110° C. Intermediate M can be reduced to the desired compound of Formula B or F by reduction, e.g. using lithium aluminum hydride, lithium borohydride or diborane as reducing agent, in an inert solvent such as tetrahydrofuran, dioxane or diethyl ether at temperatures of from about 25–100° C. Preferred is the reduction with lithium aluminum hydride in tetrahydrofuran at a temperature of about 65° C.

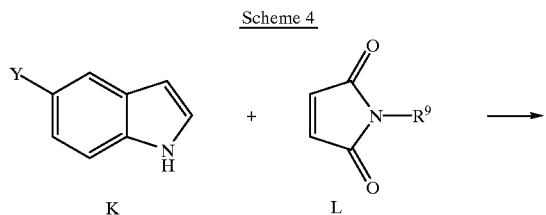

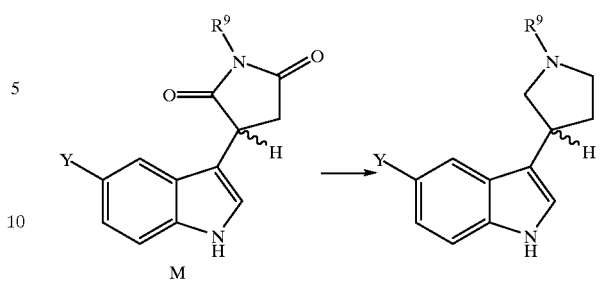

Compounds of Formula B or F wherein $R^2$ is a group of Formula III, can be prepared as shown in Scheme 5. Reagent N, in which R is, for example, benzyl or t-butyl, can be condensed with indole K, wherein Y is as defined above, typically by first converting the indole to a magnesium derivative by reaction with a suitable Grignard reagent, such as t-butyl- or ethyl-magnesium bromide, in an inert solvent. Then the magnesium derivative so formed can be reacted in situ with a reagent of Formula N to provide intermediates of Formula O. Suitable solvents include tetrahydrofuran and diethylether (which is preferred). The reaction can be conducted at temperatures ranging from −30 to 65° C., suitably at room temperature. Intermediate O can be reduced with hydride reducing agents directly to provide intermediate P wherein $R^{10}$ is methyl. The preferred reducing conditions are lithium aluminum hydride in tetrahydrofuran at a temperature of around 65° C. Alternatively, intermediate O can be deprotected under standard conditions, for example sodium hydroxide in methanol, and alkylated on the pyrrolidine nitrogen by treatment with $R^{10}$-Z, wherein $R^{10}$ is as defined in Formulae I and V and Z is a suitable leaving group such as halogen, in the presence of a base in an inert solvent to provide intermediates Q and S respectively. Suitable alkylation conditions include potassium carbonate in acetonitrile or triethylamine in dichloromethane. Temperatures can be in the range of 25 to 85° C., preferably at room temperature. Intermediate S can be reduced as described above to provide compounds of Formula P, wherein $R^{10}$ is as described in Formulae I and V.

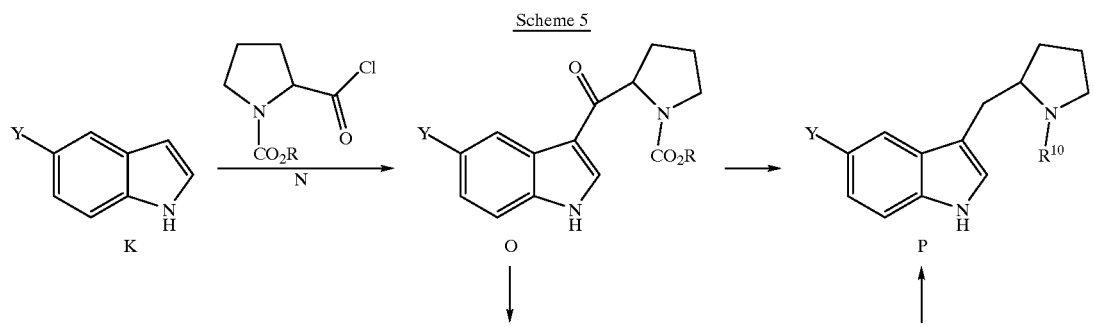

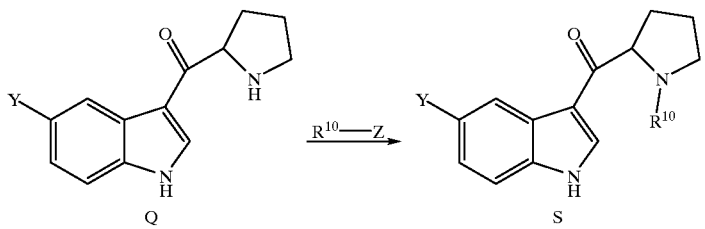

Compounds of Formulae I and V wherein $R^2$ is a group of Formula IV, can be prepared as shown in Scheme 6. Reagent T wherein $R^{11}$ is H or loweralkyl can be condensed with indole K in the presence of a base in a suitable solvent at temperatures in the range of 25 to 100°0 C., preferably, 60–90°0 C., to provide compounds of Formula U. Suitable bases include organic amine such as pyrrolidine or triethylamine and suitable solvents include methanol, ethanol and the like. The double bond of in the piperidine ring of compounds of Formula U can be reduced using standard hydrogenation conditions or using metal hydride reducing agents as described above.

Scheme 6

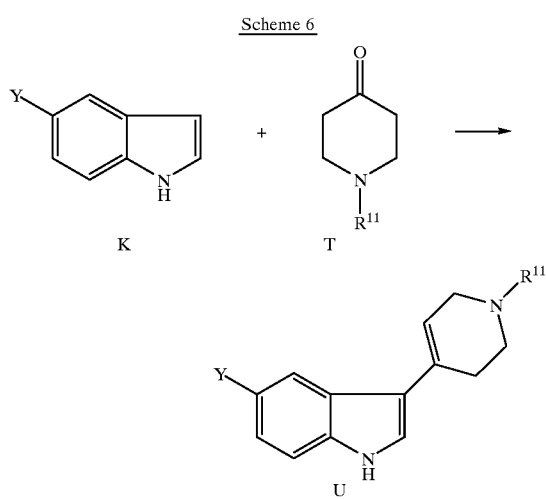

Compounds of Formulae I and V wherein $R^3$ is benzoyl, can be prepared from compounds of Formulae I and V, wherein $R^3$ is H by reaction with benzoyl chloride in an inert solvent in the presence of a base and catalyst. Suitable solvents include dichloromethane, chloroform or toluene, the base can be any organic amine and the catalyst, a pyridine derivative. Preferred conditions are triethylamine and dimethylaminopyridine (DMAP) in dichloromethane. Temperatures can be in the range of 0–40° C., preferably at room temperature. Alternatively, the benzoyl group can be introduced at an intermediate stage in the synthesis, for example at intermediates A, F, K or M, using the above procedure.

The cyclic stannanes of Formula C may be prepared using standard procedures. For example, the cyclohexenyl stannanes can be prepared, using the method of Gilbertson, et al. (Tetrahedron Lett. 1988, 29:4795), from the enol triflate and the higher order cuprate generated from tributylstannyl lithium and copper (I) cyanide. The triflate can be prepared from the corresponding ketone using lithium diisopropylamide to generate the enolate and trapping with N-phenyltriflimide as described in Zheng, et al. (Tetrahedron Lett. 1993, 34:2253). The heterocyclic stannanes can be prepared from the corresponding dihydro-derivatives by reaction with tributylstannyl chloride in the presence of a strong base in an inert solvent. Suitable strong bases include alkyl lithiums and suitable solvents include tetrahydrofuran and other ethers. Preferred conditions are t-butyllithium in tetrahydrofuran. Temperatures can be in the range of 0 to –80° C., preferably around –78° C. Reagents of Formula C which are substituted with groups selected from loweralkyl, hydroxy, loweralkoxy and loweralkoxy substituted lower alkylene can be prepared in an analogous fashion using appropriately substituted starting materials, some of which are conveniently available in the form of readily available glucals. It is understood that functional groups such as hydroxyl groups may have to be protected during certain chemical manipulations using standard protecting group procedures known to one skilled in the art.

The ketones of Formula G and T, indoles of Formula K and maleimides L are available commercially or can prepared using standard procedures.

In an aspect of the invention, the compound is provided in labeled form, such as radiolabeled form, e. g. labeled by incorporation within its structure $^3H$ or $^{14}C$ or by conjugation to $^{125}I$. In another aspect of the invention, the compounds in labeled form can be used as competitive ligands to identify 5-$HT_{1D}$-like receptor ligands by techniques common in the art. This can be achieved by incubating the receptor or tissue in the presence of a ligand candidate and then incubating the resulting preparation with an equimolar amount of radiolabeled compound of the invention such as 5-(1-aza-1-methylcyclohex-3-en-4-yl)-3-[2-(N,N-dimethylamino)ethyl]-1H-indole. 5-$HT_{1D}$-like receptor ligands are thus revealed as those that are not significantly displaced by the radiolabeled compound of the present invention. Alternatively, 5-$HT_{1D}$-like receptor ligand candidates may be identified by first incubating a radiolabeled form of a compound of the invention then incubating the resulting preparation in the presence of the candidate ligand. A more potent 5-$HT_{1D}$-like receptor ligand will, at equimolar concentration, displace the radiolabeled compound of the invention.

The present compounds are useful as pharmaceuticals for the treatment of various conditions in which the use of a 5-$HT_{1D}$-like ligand is indicated, such as for the treatment of migraine, cluster headache and portal tension, a condition characterized by increased portal vein blood flow and typically associated with cirrhosis of the liver.

For use in medicine, the compounds of the present invention can be administered in a standard pharmaceutical composition. The present invention therefore provides, in a further aspect, pharmaceutical compositions comprising a pharmaceutically acceptable carrier and at least one compound of Formula I or V, or a pharmaceutically acceptable salt, solvate or hydrate thereof, in an amount effective to treat the target indication.

The compounds of the present invention may be administered by any convenient route, for example by oral, parenteral, buccal, sublingual, nasal, rectal or transdermal administration and the pharmaceutical compositions will be formulated accordingly.

Compounds of Formulae I and V and their stereoisomers, solvates, hydrates or pharmaceutically acceptable salts for oral administration can be formulated as liquids, for example syrups, suspensions, solutions or emulsions, or as solid forms such as tablets, capsules and lozenges, or they may be presented as a dry product for constitution with water or other suitable vehicle before use. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent (e.g. sorbitol syrup, methyl cellulose or hydrogenated edible fats), preservative (e.g. methyl or propyl p-hydroxybenzoates or sorbic acid), flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

The compounds of the invention may be formulated for parenteral administration by injection, including using conventional catheterisation techniques or infusion. Formulations for injection may be presented in unit dosage form, e.g. in ampoules or in multi-dose containers, with an added preservative. Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil, and may contain formulatory agents such as suspending, stabilizing and/or dispersing agents. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fiuorochlorohydrocarbon. The aerosol dosage forms can also take the form of a pump-atomizer. Capsules and cartridges of e.g. gelatin for use in an inhaler or atomizing device may be formulated containing a powder mix of a compound of the invention and a suitable powder base such as lactose or starch.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of for example suppositories or retention enemas, containing a conventional suppository base such as cocoa butter or other glycerides.

A proposed dose of the compounds of the invention for oral, buccal, sublingual or rectal administration to human (about 70 kg body weight) for the treatment of migraine is 0.1 mg to 500 mg, for example 0.5 mg to 100 mg, preferably 1 mg to 50 mg, of active ingredient per dose which could be administered up to 8 times per day, more usually 1 to 4 times per day. It will be appreciated that it may be necessary to make routine changes to the dosage depending on the age and weight of the patent as well as the severity of the condition to be treated. It should be understood that unless otherwise indicated, the dosages are referred to in terms of the weight of the compound of Formula I or V calculated as the free base.

The overall daily dosage administered by injection may be in the range of 0.01 mg to 100 mg, preferably between 0.1 mg and 50 mg, e.g., between 1 mg and 25 mg, of a compound of Formula I or V or a pharmaceutically acceptable salt, solvate or hydrate thereof calculated as the free base, the compound being administered 1 to 4 doses per day.

Aerosol formulations are preferably arranged so that each metered dose or "puff" delivered from a pressurized aerosol contains 0.1 to 10 mg of a compound of the invention, and each dose administered via capsules and cartridges in an inhaler contains 0.1 to 50 mg of a compound of the invention. Administration may be several times daily, for example 2 to 8 times, giving for example 1, 2 or 3 doses each time. The overall daily dose by inhalation will be similar to that for oral administration.

The compounds of the invention may, if desired, be administered in combination with one or more other therapeutic agents, such as analgesics, anti-inflammatory agents and anti-nauseants.

EXAMPLE 1(a)

5-Bromo-3-(1-pyrrolidinylglyoxyl)-1H-indole

To a solution of 5-bromoindole (3.92 g, 20 mmol) in ether (50 mL), cooled to 0° C., was added a solution of oxalyl chloride in dichloromethane (2M, 10 mL) dropwise. The resulting mixture was stirred at room temperature overnight and then cooled to 0° C. and pyrrolidine (6.7 mL, 80 mmol) was added dropwise. After stirring for 2 hours at room temperature, the mixture was poured into water (50 mL) and extracted with dichloromethane (3×100 mL). The combined organic phases were dried over sodium sulfate and evaporated to a white amorphous solid which was washed with ethyl acetate (50 mL) to give the title compound (2.87 g, 45%). mp 212–213° C.; $^1$H NMR (CDCl$_3$, 300 MHz) d: 10.69 (s, 1H), 8.49 (d, J=1.5 Hz, 1H), 7.87 (d, J=3.0 Hz, 1H), 7.31 (dd, J=8.6, 1.5 Hz, 1H), 7.17 (d, J=8.6 Hz, 1H), 3.59 (m, 4H), 1.94 (m, 4H).

In a like manner, the following additional compound was prepared:

(b) 5-Bromo-3-(N,N-dimethylaminoglyoxyl 1H-indole, from dimethylamine; $^1$H NMR (CDCl$_3$, 300 MHz) d: 10.05 (s, 1H), 8.48 (d, J=1.5 Hz, 1H), 7.71 (d, J=2.4 Hz, 1H), 7.35 (dd, J=1.5, 8.5 Hz, 1H), 7.19 (d, J=8.5 Hz, 1H), 3.10 (s, 3H), 3.06 (s, 3H).

EXAMPLE 2(a)

(R)-3-(N-Benzyloxycarbonylpyrrolidin-2-ylcarbonyl)-5-bromo-1H-indole

To a stirred solution of N-benzyloxycarbonyl-R-proline (2.5 g, 10.0 mmol) in anhydrous methylene chloride was added a solution of oxalyl chloride (2M solution in methylene chloride, 7 mL, 15.0 mmol). The resulting mixture was stirred at room temperature under argon for 2 hours. The solvent and excess oxalyl chloride were evaporated under reduced pressure and the crude product washed with hexane (3×10 mL) and evaporated to dryness to provide N-benzyloxycarbonyl-R-proline acid chloride which was used directly for the next reaction.

N-Benzyloxycarbonyl-R-proline acid chloride from the above reaction was dissolved in anhydrous diethyl ether (30 mL) and added at 0° C. to a solution of 5-bromoindole (2.9 g, 15.0 mmol) and t-butylmagnesium chloride (2M solution in diethyl ether, 8.3 mL, 16.5 mmol) in anhydrous diethyl ether (30 mL). The resulting mixture was stirred at room temperature under argon for 45 minutes and then ethyl acetate (150 mL) and saturated sodium bicarbonate (30 mL) were added. The organic layer was dried and evaporated under reduced pressure to provide a yellow oil. The title compound was crystallized using hexane/ethyl acetate (9:1) to provide a white solid (3.07 g, 72%). mp 95–96° C.

In a like manner the following additional compound was prepared:

(b) (S)-3-(N-Benzyloxycarbonylpyrrolidin-2-ylcarbonyl)-5-bromo-1H-indole, from N-benzyloxycarbonyl-S-proline; mp 95–96° C.

EXAMPLE 3(a)

5-Bromo-3-[2-(N,N-dimethylamino)ethyl]-1H-indole

A solution of LAH (39 mL, 1M in THF, 39 mmol) was added slowly to a cooled (0° C.) solution of 5-bromo-3-(N,N-dimethylaminoglyoxyl)-1H-indole (Example 1b, 2.82 g, 9.5 mmol) in THF (100 mL). Once the addition was completed, the reaction mixture was stirred at reflux overnight prior to quenching with sodium sulfate decahydrate. The product was taken into ethyl acetate, filtered to remove the solid residue, and the solvent was removed in vacuo. The product was used as is for the next reaction.

In a like manner, the following additional compounds were prepared:

(b) 5-Bromo-3-(2-pyrrolidinylethyl)-1H-indole: (72%) from 5-bromo-3-(1-pyrrolidinylglyoxyl)-1H-indole (Example 1a).

(c) (S)-5-Bromo-3-[(N-methylpyrrolidin-2-yl)methyl]-1H-indole: (57%) from (S)-3-(N-benzyloxycarbonylpyrrolidin-2-ylcarbonyl)-5-bromo-1H-indole (Example 2b).

(d) (R)-5-Bromo-3-[(N-methylpyrrolidin-2-yl)methyl]-1H-indole: (63%) from (R)-3-(N-benzyloxycarbonylpyrrolidin-2-ylcarbonyl5-bromo-1H-indole (Example 2a).

EXAMPLE 4

5-Bromo-3-(N-methylpyrrolidin-3-yl)-1H-indole

To a solution of 5-bromoindole (5 g, 25.5 mmol) in glacial acetic acid (60 mL) was added N-methylmaleimide (6.1 g, 56.11 mmol) and the resulting mixture was heated to reflux for 4 days. The acetic acid was removed by distillation and the crude product was dissolved in diethyl ether (500 mL) and washed with saturated sodium bicarbonate (2×100 mL) and brine (3×100 mL). The solvent was evaporated and the residue chromatographed on silica gel using hexane/ethyl acetate (1:1) as the eluent to provide 3-(5-bromo-1H-indol-3-yl)-N-methylsuccinimide (5.85 g, 75%) which was used directly for the next reaction. Yellow solid, mp 194–195° C.

To a stirred solution of 3-(5-bromo-1H-indol-3-yl)-N-methylsuccinimide (1.3 g, 4.2 mmol) in anhydrous tetrahydrofuran (12 mL) at 0° C., was added lithium aluminum hydride (1M solution in tetrahydrofuran, 9.3 mL, 9.3 mmol).

The resulting mixture was heated to reflux under argon for 2 hours, then cooled to 0° C. and quenched with cold water (2 mL) and ammonium hydroxide (15 mL). The resulting solution was stirred at room temperature for 1 hour and then filtered through celite. The filtrate was evaporated to dryness and the crude product extracted into ethyl acetate (250 mL). The solvent was once again evaporated and the product purified by silica gel chromatography using chloroform/ammonia (2M in methanol) (9:1) as the eluent to provide the title compound as a white solid (0.700 g, 64%). mp 152–154° C.; HRMS (FAB): MH$^+$ for $C_{13}H_{15}{}^{79}BrN_2$, calculated 279.0496, found 279.0478.

EXAMPLE 5(a)

5-Bromo-3-[2-(N,N-dimethylamino)ethyl]-1-benzoylindole

Benzoyl chloride (1.7 mL, 14.6 mmol) was added to a solution of 5-bromo-3-[2-(N,N-dimethylamino)ethyl]-1H-indole (Example 3a, 9.5 mmol) in dichloromethane (70 mL) containing triethylamine (4 mL, 28.7 mmol) and DMAP (206 mg, 1.7 mmol). The resulting solution was stirred at room temperature for 20 h. Dilution with dichloromethane (500 mL) was followed by sequential washing with water (200 mL) and brine (150 mL), drying over sodium sulfate and removal of the solvent in vacuo. Flash chromatography (silica gel, 3–5% 2M methanolic ammonia in dichloromethane) yielded 5-bromo-3-[2-(N,N-dimethylamino)ethyl]-1-benzoylindole (2.95 g, 84%).

In a like manner, the following additional compounds were prepared:

b) 5-Bromo-3-(N-methylpyrrolidin-3-yl)-1-benzoylindole: (0.595 g, 58%) from 5-bromo-3-(N-methylpyrrolidin-3-yl)-1H-indole (Example 4, 0.749 g, 2.68 mmol), benzoyl chloride (0.42 g, 3.00 mmol), triethylamine (0.55 g, 5.44 mmol) and DMAP (0.07 g, 0.54 mmol) in CH$_2$Cl$_2$ (20 ml); yellow oil.

c) 5-Bromo-3-(2-pyrrolidinylethyl)-1-benzoylindole: (75%), from 5-bromo-3-(2-pyrrolidinylethyl)-1H-indole (Example 3b).

d) (S)-5-Bromo-3-[(N-methylpyrrolidin-2-yl)methyl]-1-benzoylindole: (39%), from (S)-5-Bromo-3-[(N-methylpyrrolidin-2-yl)methyl]-1H-indole (Example 3c).

e) (R)-5-Bromo-3-[(N-methylpyrrolidin-2-yl)methyl]-1-benzoylindole: (76%), from (R)-5-Bromo-3-[(N-methylpyrrolidin-2-yl)methyl]-1H-indole (Example 3d).

EXAMPLE 6

2-Tributylstannyl-2,3-dihydropyran

To a solution of 2,3-dihydropyran (2.0 g, 23.8 mmol) in dry THF (50 mL) was added tert-BuLi (26.2 mmol) at −78° C. and the resulting solution was stirred at 0° C. for 1 hour. The mixture was cooled to −78° C. and tributylstannyl chloride (5.53 g, 17.0 mmol) was added and stirring was continued for fifteen minutes at which time the reaction mixture was diluted with water and extracted 3× with ethyl acetate. The organic layer was washed with brine, dried (MgSO$_4$), filtered and concentrated. The crude product was filtered through a plug of silica gel to yield 5.23 g (59%) of the title compound as a clear liquid.

EXAMPLE 7

Tri-O-methoxy-D-glucal

To a solution of tri-O-acetyl-D-glucal (5.05 g, 18.6 mmol) in methanol (15 mL) was added NH$_3$ (2M in MeOH) (5 mL)

and the mixture was allowed to stir for 6 hours. At this time, the solvent was evaporated and anhydrous THF was added (25 mL) followed by sodium hydride (1.43 g, 59.4 mmol). The mixture was heated at reflux for 1 hour and then allowed to cool to room temperature. Methyl iodide was added (8.43 g, 59.4 mmol) and the mixture was allowed to stir overnight. Water was added and the product was extracted with ethyl acetate three times. The organic layer was washed with brine, dried ($NaSO_4$) and concentrated. The crude product was purified by column chromatography (5% $NH_3$ in $CH_2Cl_2$) to yield the title compound (1.82 g, 52%) as a yellow liquid.

EXAMPLE 8

1-Tributylstannyl-tri-O-methoxy-D-glucal

To a solution of potassium tert-butoxide (0.42 g, 3.75 mmol) in anhydrous THF (10 mL) was added "BuLi (4.13 mmol) at −78° C. After 15 minutes, tri-O-methoxy-D-glucal (Example 7, 0.194 g, 1.03 mmol) was added in THF (5 mL). After stirring for one hour, tributylstannyl chloride was added and the mixture was allowed to warm to room temperature at which time it was cooled to 0° C. and quenched with ammonium chloride (sat.) and extracted with ethyl acetate three times. The organic layer was washed with water and brine, dried ($NaSO_4$), filtered and concentrated to yield the title compound (0.24 g, 49%) as a clear liquid.

EXAMPLE 9(a)

5-(Cyclohex-1-en-1-yl)-3-[2-(N,N-dimethylamino) ethyl]-1H-indole

Method 1:

A solution of 5-bromo-3-(N,N-dimethylaminoglyoxyl)-1H-indole (Example 1b, 103.9 mg, 0.35 mmol), 1-tributylstannylcyclohex-1-ene (130 mg, 0.35 mmol) and tetrakistriphenyphosphine palladium (39 mg, 0.034 mmol) in anhydrous DMF (3 mL) was stirred at 100–105° C. for 3 days. After cooling to room temperature, the product was taken into ethyl acetate, filtered through celite, washed with water (2x) and brine (1x), dried over sodium sulfate and the solvent was removed in vacuo. Flash chromatography on silica gel (65–100% ethyl acetate in hexanes) yielded 5-(cyclohex-1-en-1-yl)-3-(N,N-dimethylaminoglyoxyl)-1H-indole (35 mg).

A solution of LAH (0.25 mL, 1M in THF, 0.25 mmol) was added slowly to a cooled (0° C.) solution of the glyoxyl amide (35 mg, 0.12 mmol) in THF (2.5 mL). Once the addition was completed, the reaction mixture was stirred at reflux for 2h prior to quenching with sodium sulfate decahydrate. The product was taken into ethyl acetate, filtered to remove the solid residue, and the solvent was removed in vacuo. Purification by preparative thin layer chromatography on silica gel eluting with 5% 2M methanolic ammonia in dichloromethane yielded 5-(cyclohex-1-en-1-yl)-3-[2-(N, N-dimethylamino)ethyl]-1H-indole (12 mg, 13% over 2 steps); $HRMS-FAB^+$ for $C_{18}H_{24}N_2$: calculated $MH^+$:269.20178; found $MH^+$:269.20097.

Method 2:

A solution of 5-bromo-3-[2-(N,N-dimethylamino)ethyl]-1-benzoylindole (Example 5a, 109.8 mg 0.30 mmol), 1-tributylstannylcyclohex-1-ene (111 mg, 0.30 mmol) and tetrakistriphenyphosphine palladium (80 mg, 0.07 mmol) in toluene (2 mL) was stirred at 100–110° C. overnight. After removal of the solvent in vacuo, flash chromatography on silica gel (2–10% 2M methanolic ammonia in dichloromethane) yielded 5-(cyclohex-1-en-1-yl)-3-[2-(N, N-dimethylamino)ethyl]-1-benzoylindole (31 mg, 28%).

An aqueous solution of sodium hydroxide (2M, 0.75 mL, 1.5 mmol) was added to 5-(cyclohex-1-en-1-yl)-3-[2-(N,N-dimethylamino)ethyl]-1-benzoylindole (31 mg, 0.08 mmol) in methanol (1.5 mL) and the resulting solution was stirred at reflux for 16 h. The reaction mixture was diluted with water and the methanol was removed in vacuo. The product was extracted into dichloromethane (5x), which was then washed with brine and dried over sodium sulfate and the solvent was removed in vacuo. Preparative thin layer chromatography (silica gel, 7% 2M methanolic ammonia in dichloromethane) yielded 5-(cyclohex-1-en-1-yl)-3-[(2-(N, N-dimethylamino)ethyl]-1H-indole (9.7 mg, 43%).

In a like manner, the following additional compound was prepared:

(b) 3-[2-(N,N-Dimethylamino)ethyl]-5-(tetrahydropyran-2-yl)-1H-indole: According to method 1 from 5-bromo-3-(N,N-dimethylaminoglyoxyl)-1H-indole (Example 1b, 150 mg, 0.52 mmol), 2-tributylstannyl-2,3-dihydropyran (240 mg, 0.64 mmol) and tetrakistriphenyphosphine palladium (60 mg, 0.05 mmol) in anhydrous DMF (3 mL) at 100–105° C. overnight. Flash chromatography on silica gel (5% 2M methanolic ammonia in dichloromethane) provided 5-(2,3-dihydropyran-2-yl)-3-(N,N-dimethylaminoglyoxyl)-1H-indole (34.6 mg, 24%). A solution of LAH (0.42 mL, 1M in THF, 0.42 mmol) was added slowly to a cooled (0° C.) solution of the 5-(2,3-dihydropyran-2-yl)-3-(N,N-dimethylaminoglyoxyl)-1H-indole (30 mg, 0.11 mmol) in THF (1 mL). Flash chromatography (silica gel, 5% 2M methanolic ammonia in dichloromethane) yielded 3-[2-(N, N-dimethylamino)ethyl]-5-(tetrahydropyran-2-yl)-1H-indole (3.6 mg, 13%).

EXAMPLE 10

(S)-5-(1-Aza-1-tert-butoxycarbonylcyclohex-3-en-4-yl)-3-[(N-methylpyrrolidin-2-yl)methyl]-1H-indole A solution of (S)-5-bromo-3-[(N-methylpyrrolidin-2-yl)methyl]-1-benzoylindole (Example 5d, 149.8 mg, 0.38 mmol), 4-tributylstannyl-1-aza-1-tert-butoxycarbonylcyclohex-3-ene (108 mg, 0.23 mmol) and tetrakistriphenyphosphine palladium (41 mg, 0.035 mmol) in toluene (2 mL) was stirred at 100–110° C. A second portion of tetrakistriphenyphosphine palladium was added after 1 h and heating was continued overnight. After removal of the solvent in vacuo, flash chromatography on silica gel (5–10% 2M methanolic ammonia in chloroform) yielded (S)-5-(1aza-1-tert-butoxycarbonylcyclohex-3-en-4-yl)-3-[(N-methylpyrrolidin-2-yl)methyl]-1-benzoylindole (60 mg, 52%).

An aqueous solution of sodium hydroxide (2M, 1 mL, 2 mmol) was added to (S)-5-(1-aza-1-tert-butoxycarbonylcyclohex-3-en-4-yl)-3-[(N-methylpyrrolidin-2-yl)methyl]-1-benzoylindole (55 mg, 0.11 mmol) in methanol (2 mL) and the resulting solution was stirred at reflux for 15 h. The reaction mixture was diluted with water (10 mL) and the methanol was removed in vacuo. The product was extracted into dichloromethane (5x), which was then washed with brine and dried over sodium sulfate. Flash chromatography (silica gel, 7% 2M methanolic ammonia in dichloromethane) yielded (S)-5-(1-aza-1-tert-butoxycarbonylcyclohex-3-en-4-yl)-3-[(N-methylpyrrolidin-2-yl)methyl]-1H-indole (18.2 mg, 42%); $HRMS-FAB^+$ for $C_{24}H_{33}N_3O_2$: calculated $MH^+$:396.26511; found $MH^+$:396.26355.

EXAMPLE 11

5-(1-Aza-1-tert-butoxycarbonylcyclohex-3-en-4-yl)-3-[2-(N,N-dimethylamino)ethyl]-1H-indole A solution of 5-bromo-3-[2-(N,N-dimethylamino)ethyl]-1-benzoylindole (Example 5a, 310 mg 0.84 mmol), 4-tributylstannyl-1-aza-1-tert-butoxycarbonylcyclohex-3-ene (400 mg, 0.85 mmol) and tetrakistriphenyphosphine palladium (200 mg, 0.17 mmol) in toluene (6 mL) was stirred at 100–110° C. overnight. After removal of the solvent in vacuo, flash chromatography on silica gel (2–10% 2M methanolic ammonia in dichloromethane) yielded 5-(1aza-1-tert-butoxycarbonylcyclohex-3-en-4-yl)-3-[2-(N,N-dimethylamino)ethyl]-1-benzoylindole (77.2 mg, 19%).

An aqueous solution of sodium hydroxide (2M, 1.5 mL, 3 mmol) was added to 5-(1-aza-1-tert-butoxycarbonylcyclohex-3-en-4-yl)-3-[2-(N,N-dimethylamino)ethyl]-1-benzoylindole (77 mg, 0.16 mmol) in methanol (3 mL) and the resulting solution was stirred at reflux for 17 h. The reaction mixture was diluted with water (10 mL) and the methanol was removed in vacuo. The product was extracted into dichloromethane (5×), which was then washed with brine and dried over sodium sulfate and the solvent was removed in vacuo. Preparative thin layer chromatography (silica gel, 7% 2M methanolic ammonia in dichloromethane) yielded 5-(1-aza-1-tert-butoxycarbonylcyclohex-3-en-4-yl)-3-[(2-(N,N-dimethylamino)ethyl]-1H-indole (30.8 mg, 52%); HRMS-FAB$^+$ for $C_{22}H_{21}N_3O_2$: calculated MH$^+$:370.24945; found MH$^+$:370.24866.

EXAMPLE 12

5-(3,4-Dihydropyran-4-yl)-3-[2-(N,N-dimethylamino)ethyl]-1H-indole

A solution of 5-bromo-3-[2-(N,N-dimethylamino)ethyl]-1-benzoylindole (Example 5a, 180 mg 0.48 mmol), 4-tributylstannyl-3,4-dihydropyran (180 mg, 0.48 mmol) and tetrakistriphenyphosphine palladium (118 mg, 0.1 mmol) in toluene (3 mL) was stirred at 100–110° C. A second portion of catalyst was added after 1 h and heating was continued overnight. After removal of the solvent in vacuo, flash chromatography on silica gel (2–6% 2M methanolic ammonia in dichloromethane) yielded 5-(3,4-dihydropyran-4-yl)-3-[2-(N,N-dimethylamino)ethyl]-1-benzoylindole (30.5 mg, 17%).

An aqueous solution of sodium hydroxide (2M, 1 mL, 2 mmol) was added to 5-(3,4-dihydropyran-4-yl)-3-[2-(N,N-dimethylamino)ethyl]-1-benzoylindole (30 mg, 0.08 mmol) in methanol (2 mL) and the resulting solution was stirred at room temperature for 16 h. The reaction mixture was partitioned between water and ethyl acetate, washed with brine, dried over sodium sulfate and the solvent was removed in vacuo. Preparative thin layer chromatography (silica gel, 10% 2M methanolic ammonia in dichloromethane) yielded 5-(3,4-dihydropyran-4-yl)-3-[2-(N,N-dimethylamino)ethyl]-1H-indole (15.3 mg, 70%); HRMS-FAB$^+$ for $C_{17}H_{22}N_2O$: calculated MH$^+$:271.18103; found MH$^+$:271.18177.

EXAMPLE 13(a)

5-(1-Hydroxycyclohex-1-yl)-3-(2-pyrrolidinylethyl)-1H-indole

A solution of 5-bromo-3-(2-pyrrolidinylethyl)-1H-indole (Example 3b, 303 mg, 1.03 mmol) in ether (12.5 mL) was added to KH (42.9 mg, 1.07 mmol) at 0° C. After stirring at 0° C. for 20 minutes, the reaction mixture was cooled to −78° C. and a solution of tert-butyllithium in pentane (1.7 M, 0.22 mL, 2.1 mmol) was added dropwise. The reaction mixture was stirred at −78° C. for 30 minutes prior to the addition of cyclohexanone (0.22 mL, 2.1 mmol). The reaction was quenched by the addition of pH 7 buffer and the product was extracted into ethyl acetate, washed with water and brine, and dried over sodium sulfate. After removal of the solvent in vacuo, flash chromatography (silica, 5–10% 2M methanolic ammonia in dichloromethane) yielded 5-(1-hydroxycyclohex-1-yl)-3-(2-pyrrolidinylethyl)-1H-indole (116.4 mg, 36%); HRMS-FAB$^+$ for $C_{20}H_{28}N_2O$: calculated MH$^+$:313.22800; found MH$^+$:313.23151.

In a like manner, the following additional compounds were prepared:

(b) 5-(1-Aza-1-benzyl-4-hydroxycyclohex-4-yl)-3-(2-pyrrolidinylethyl)-1-H-indole: (322.2 mg, 37%) from 5-bromo-3-(2-pyrrolidinylethyl)-1H-indole (Example 3b, 632 mg, 2.16 mmol), KH (86.4 mg, 2.15 mmol) in ether (25 mL) and THF (5 mL) with tert-butyllithium in pentane (1.7 M, 2.77 mL, 4.7 mmol) and N-benzylpiperidinone (0.87 mL, 4.7 mmol); beige solid, mp 143–147° C.; HRMS-FAB$^+$ for $C_{26}H_{33}N_3O$: calculated MH$^+$:404.27020; found MH$^+$:404.26676.

(c) 5-(1-Aza-1-tert-butoxycarbonyl-4-hydroxycyclohex-4-yl)-3-(2-pyrrolidinylethyl)-1H-indole: (147.9 mg, 21%) from 5-bromo-3-(2-pyrrolidinylethyl)-1H-indole (Example 3b, 503.4 mg, 1.72 mmol), KH (69.3 mg, 1.73 mmol) in ether (15 mL) and THF (5 mL) with tert-butyllithium in pentane (1.7 M, 2.22 mL, 3.8 mmol) and N-tert-butoxycarbonylpiperidinone (753 mg, 3.8 mmol); HRMS-FAB$^+$ for $C_{24}H_{35}N_3O_3$: calculated MH$^+$:414.27567; found MH$^+$:414.27300.

(d) 5-(1-Aza-1-methyl-4-hydroxycyclohex-4-yl)-3-(2-pyrrolidinylethyl)-1H-indole: (166.1 mg, 37%) from 5-bromo-3-(2-pyrrolidinylethyl)-1H-indole (Example 3b, 403 mg, 1.37 mmol), KH (55.1 mg, 1.37 mmol) in THF (5 mL) with tert-butyllithium in pentane (1.7 M, 2.0 mL, 3.4 mmol) and N-methylpiperidinone (0.40 mL, 3.2 mmol); white solid, decomposition or phase change at 155° C., sharp mp 179–182° C.

(e) 5-(1-Aza-1-methyl-4-hydroxycyclohex-4-yl)-3-[2-(N,N-dimethylamino)ethyl]-1H-indole: (522 mg, 20%) from 5-bromo-3-[2-(N,N-dimethylamino)ethyl]-1H-indole (Example 3a, 2.39 g, 8.9 mmol), KH (377 mg, 9.4 mmol) in THF (40 mL) with tert-butyllithium in pentane (1.7 M, 12.5 mL, 21.2 mmol) and N-methylpiperidinone (3 mL, 24.4 mmol) with the exception that filtration from dichloromethane replaced the flash chromatographic purification in this example; beige solid, decomposition or phase change at 120° C., sharp mp 172–175° C.; HRMS-FAB$^+$ for $C_{18}H_{27}N_3O$: calculated MH$^+$:302.22375; found MH$^+$:302.22538.

(f) 3-[2-(N,N-Dimethylamino)ethyl]-5-(4-hydroxytetrahydropyran-4-yl)-1H-indole: (30%) from 5-bromo-3-[2-(N,N-dimethylamino)ethyl]-1H-indole (Example 3a); mp 166–168° C. (changes at 145–148° C.); HRMS-FAB$^+$ for $C_{17}H_{25}N_2O_2$: calculated MH$^+$:289.19159; found MH$^+$:289.19074.

g) 5-(4-Hydroxytetrahydropyran-4-yl)-3-(2-pyrrolidinylethyl)-1H-indole: (35%) from 5-bromo-3-(2-pyrrolidinylethyl)-1H-indole (Example 3b); mp 49–52° C.; HRMS-FAB$^+$ for $C_{19}H_{27}N_2O_2$: calculated MH$^+$:315.20724; found MH$^+$:315.20968.

h) 3-[2-(N,N-Dimethylamino)ethyl]-5-(4-hydroxythiapyran-4-yl)-1H-indole: (34%) from 5-bromo-3-[2-(N,N-dimethylamino)ethyl]-1H-indole (Example 3a); mp 156–159° C. (with decomp., changes at 137° C.); HRMS-FAB$^+$ for $C_{17}H_{25}N_2OS$: calculated MH$^+$:305.16876; found MH$^+$:305.17147.

(i) 5-(4-Hydroxythiapyran-4-yl)-3-(2-pyrrolidinylethyl)-1H-indole: (56%) from 5-bromo-3-(2-pyrrolidinylethyl)-

1H-indole (Example 3b); mp 66–78° C.; HRMS-FAB⁺ for $C_{19}H_{27}N_2OS$: calculated MH⁺:331.18442; found MH⁺:331.18568.

EXAMPLE 14(a)

5-(Cyclohex-1-en-1-yl)-3-(2-pyrrolidinylethyl)-1H-indole

Methanesulfonyl chloride (0.042 mL, 0.54 mmol) was added to a solution of 5-(1-hydroxycyclohex-1-yl)-3-(2-pyrrolidinylethyl)-1H-indole (Example 13a, 50.6 mg, 0.16 mmol) and triethylamine (0.15 mL, 1.06 mmol) in dichloromethane (2.5 mL) at 0° C. The reaction was allowed to warm slowly to room temperature and stirring was continued overnight. The reaction mixture was diluted with dichloromethane (100 mL) and washed sequentially with water and brine, dried over sodium sulfate and the solvent was removed in vacuo. Flash chromatography (silica, 5–8% 2M methanolic ammonia in dichloromethane) yielded 5-(cyclohex-1-en-1-yl)-3-(2-pyrrolidinylethyl)-1H-indole (21.8 mg, 46%); HRMS-FAB⁺ for $C_{20}H_{26}N_2$:calculated MH⁺:295.21744; found MH⁺:295.21953.

In a like manner the following additional compounds were prepared:

(b) 5-(1-Aza-1-benzylcyclohex-3-en-4-yl)-3-(2-pyrrolidinylethyl)-1H-indole: (30 mg, 31%) from 5-(1-aza-1-benzyl-4-hydroxycyclohex-4-yl)-3-(2-pyrrolidinylethyl)-1H-indole (Example 13b, 100.1 mg, 0.25 mmol), triethylamine (0.23 mL, 1.65 mmol) and MsCl (0.065 mL, 0.84 mmol) in dichloromethane (7 mL).

(c) 5-(1-Aza-1-methylcyclohex-3-en-4-yl)-3-(2-pyrrolidinylethyl)-1H-indole: (17.6 mg, 13%) from 5-(1-aza-1-methyl-4-hydroxycyclohex-4-yl)-3-(2-pyrrolidinylethyl)-1H-indole (Example 13d, 145 mg, 0.44 mmol), triethylamine (0.95 mL, 6.8 mmol) and MsCl (0.25 mL, 3.2 mmol) in dichloromethane (3.5 mL) and THF (7 mL) with the exception that the reaction was carried out at a gentle reflux overnight and the extraction solvent consisted of a mixture of dichloromethane, chloroform, and ethyl acetate. Starting material (17 mg) was also recovered. The product in this case was converted to the hydrochloride salt which was soluble in methanol; HRMS-FAB⁺ for $C_{20}H_{27}N_3$: calculated MH⁺:310.22833; found MH⁺:310.22650.

EXAMPLE 15(a)

5-(1-Aza-1-benzylcyclohex-3-en-4-yl)-3-(2-pyrrolidinylethyl)-1H-indole

Trifluoroacetic acid (0.21 mL, 2.7 mmol) was added to a suspension of 5-(1-aza-1-benzyl-4-hydroxyclohex-4-yl)-3-(2-pyrrolidinylethyl)-1H-indole (Example 13d, 103.9 mg, 0.26 mmol) in tetrahydrofuran (5 mL) at 0° C. The reaction mixture was heated at 60° C. overnight. After cooling to room temperature, the solvent was removed in vacuo, and Amberlite 400(OH—) was added to a methanol solution of the product (to pH 9–10). The resin was removed by filtration and the solvent was removed in vacuo. Flash chromatography (silica gel, 5–8% 2M methanolic ammonia in dichloromethane) yielded 5-(1-aza-1-benzylcyclohex-3-en-4-yl)-3-(2-pyrrolidinylethyl)-1H-indole (82 mg, 82%, identical by NMR and tlc to product formed via mesylation).

In a like manner, the following additional compounds were prepared:

(b) 5-(3,4-dihydropyran-4-yl)-3-(2-pyrrolidinylethyl)-1H-indole: (51%) from 5-(4-hydroxytetrahydropyran-4-yl)-3-(2-pyrrolidinylethyl)-1H-indole (Example 13g); HRMS-FAB⁺ for $C_{19}H_{25}N_2O$: calculated MH⁺:297.19669; found MH⁺:297.19657.

(c) 3-(2-Pyrrolidinylethyl)-5-(3,4-dihydrothiapyran-4-yl)-1H-indole: (46%) from 5-(4-hydroxythiapyran-4yl)-3-(2-pyrrolidinylethyly-1H-indole (Example 13i); HRMS-FAB⁺ for $C_{19}H_{25}N_2S$: calculated MH⁺:313.17386; found MH⁺:313.17947.

(d) 3-[2-(N,N-Dimethylamino)ethyl]-5-(3,4-dihydrothiapyran-4-yl)-1H-indole: (50%) from 3-[2-(N,N-dimethylamino)ethyl]-5-(4-hydroxythiapyran-4-yl)-1H-indole (Example 13h); HRMS-FAB⁺ for $C_{19}H_{25}N_2S$: calculated MH⁺:287.15820; found MH⁺:287.16092.

EXAMPLE 16

5-(1-Aza-1-methylcyclohex-3-en-4-yl)-3-[2-(N,N-dimethylamino)ethyl]-1H-indole

A solution of LAH (0.15 mL, 1M in THF, 0.15 mmol) was added slowly to a solution of 5-(1-aza-1-tert-butoxycarbonylcyclohex-3-en-4-yl)-3-[2-(N,N-dimethylamino)ethyl]-1H-indole (Example 11, 13.6 mg, 0.037 mmol) in THF (1.5 mL). Once the addition was completed, the reaction mixture was stirred at reflux for 3 h prior to quenching with sodium sulfate decahydrate. The product was taken into ethyl acetate, filtered to remove the solid residue, and the solvent was removed in vacuo. Flash chromatography (silica gel, 5–10% 2M methanolic ammonia in dichloromethane) yielded 5-(1-aza-1-methylcyclohex-3-en-4-yl)-3-[2-(N,N-dimethylamino)ethyl]-1H-indole (5.3 mg, 50%); HRMS-FAB⁺ for $C_8H_{25}N_3$:calculated MH⁺:284.21268; found MH⁺:284.21389.

EXAMPLE 17(a)

5-Cyclohexyl-3-[2-(N,N-dimethylamino)ethyl]-1H-indole 5-(Cyclohex-1-en-1-yl)-3-[2-(N,N-dimethylamino)ethyl]-1H-indole (Example 9a, 8.4 mg, 0.031 mmol) in ethyl acetate (2 mL) containing a spatula tip of Pd/C (10%) was stirred at room temperature under an atmosphere of hydrogen for 5 h. The crude product was filtered through celite using 10% 2M methanolic ammonia in dichloromethane to rinse. Evaporation of the solvent in vacuo yielded 5-cyclohexyl-3-[2-(N,N-dimethylamino)ethyl]-1H-indole (6.8 mg, 81%); HRMS-FAB⁺ for $C_{18}H_{26}N_2$:calculated MH⁺:271.21744; found MH⁺:271.21692.

In a like manner, the following additional compounds were prepared:

(b) 5-Cyclohexyl-3-(2-pyrrolidinylethyl)-1H-indole: (8.0 mg, 75%) from 5-(cyclohex-1-en-1-yl)-3-(2-pyrrolidinylethyl)-1H-indole (Example 14a, 10.7 mg, 0.036 mmol) in ethyl acetate (3 mL); HRMS-FAB⁺ for $C_{20}H_{28}N_2$: calculated MH⁺:297.23306; found MH⁺:297.23120.

(c) 5-(1-Aza-1-benzylcyclohex-4-yl)-3-(2-pyrrolidinylethyl)-1H-indole:(4.5 mg, 21%) from 5-(1-aza-1-benzylcyclohex-3-en-4-yl)-3-(2-pyrrolidinylethyl]-1H-indole (Example 14b, 21.1 mg, 0.055 mmol) in ethyl acetate (2 mL) and ethanol (2 mL).

(d) (S)-5-(1-Aza-1-tert-butoxycarbonylcyclohex-4-yl)-3-[(N-methylpyrrolidin-2-yl)methyl]-1H-indole:(9.8 mg, 91%) from (S)-5-(1-aza-1-tert-butoxycarbonylcyclohex-3-en-4-yl)-3[(-N-methylpyrrolidin-2-yl)methyl]-1H-indole (Example 10, 10.6 mg, 0.027 mmol) in ethyl acetate (2 mL);

HRMS-FAB+ for $C_{24}H_{35}N_3O_2$:calculated MH+:398.28076; found MH+:398.28090.

(e) 5-(1-Aza-1-tert-butoxycarbonylcyclohex-4-yl)-3-[2-(N,N-dimethylamino)ethyl]-1H-indole:(11.1 mg,85%) from 5-(1-aza-1-tert-butoxycarbonyleyclohex-3-en-4-yl)-3-[2-(N,N-dimethylamino)ethyl]-1H-indole (Example 11, 12.9 mg, 0.035 mmol) in ethyl acetate (2 mL); HRMS-FAB+ for $C_{22}H_{33}N_3O_2$:calculated MH+:372.2651 1; found MH+:372.26070.

(f) 3-[2-(N,N-Dimethylamino)ethyl]-5-(tetrahydropyran-4-yl)-1H-indole:(7 mg, 78%) from 5-(3,4-dihydropyran-4-yl)-3-[2-(N,N-dimethylamino)ethyl]-1H-indole (Example 12, 9 mg, 0.033 mmol) in ethyl acetate (3 mL) and methanol (1 mL).

(g) 5-(1-Azacyclohexyl-3-(2-pyrrolidinylethyl)-1H-indole:(3.0 mg, 18%) as a side product from 5-(1-aza-1-benzylcyclohex-3-en-4-yl)-3-(2-pyrrolidinylethyl)-1H-indole (Example 14b, 21.1 mg, 0.055 mmol) in ethyl acetate (2 mL) and ethanol (2 mL).

(h) 5-(tetrahydropyran-4-yl)-3-(2-pyrrolidinylethyl)-1H-indole:(87%) from 5-(3,4-dihydropyran-4-yl)-3-(2-pyrrolidinylethyl)-1H-indole (Example 15a); HRMS-FAB+ for $C_{19}H_{27}N_2O$: calculated MH+:299.21234; found MH+:299.21344.

(i) 3-[2-(N,N-Dimethylamino)ethyl]-5-(1-thiacyclohex-4-yl)-1H-indole:(65% using 2M methanolic ammonia solvent with $H_2$, Pd-C) from 3-[2-(N,N-Dimethylamino)ethyl]-5-(3,4-dihydrothiapyran-4-yl)-1H-indole (Example 15c); HRMS-FAB+ for $C_{17}H_{25}N_2S$: calculated MH+:289.17386; found MH+:289.17609.

(j) 5-(1-Aza-1-methylcyclohex-4-yl)-3-[2-(N,N-dimethylamino)ethyl]-1H-indole: (74%) from 5-(1-aza-1-methylcyclohex-3-en-yl)-3-[2-(N,N-dimethylamino)ethyl]-1H-indole (Example 16); HRMS-FAB+ for $C_{18}H_{28}N_3$: calculated MH+:286.22833; found MH+:286.22703.

EXAMPLE 18(a)

5-(2,3-Dihydropyran-2-yl)-3-(N-methylpyrrolidin-3-yl)-1-benzoylindole

To a stirred solution of 2-tributylstannyl-2,3-dihydropyran (Example 6, 0.41 g, 0.11 mmol) in anhydrous toluene (15 mL) was added 5-bromo-3-(N-methylpyrrolidin-3-yl)-1-benzoylindole (Example 5b, 0.280 g, 0.729 mmol) and Pd[PPh_3]_4 (0.09 g, 0.076 mmol). The mixture was heated to reflux for 6.5 hours, cooled, filtered through celite and concentrated by reduced pressure. The crude product was purified by column chromatography [95:5 $CH_2Cl_2$: $NH_3$ (2M in MeOH)] to yield the title compound (0.241 g, 85%) as a yellow oil; HRMS-FAB+ for $C_{25}H_{26}N_2O_2$; calc. MH+:387.2072; found MH+:387.2092.

In a like manner, the following additional compounds were prepared:

b) 5-(2,3-Dihydropyran-2-yl)-3-(2-pyrrolidinylethyl)-1-benzoylindole:(75%), from 5-bromo-3-(2-pyrrolidinylethyl)-1-benzoylindole (Example 5c).

c) (S)-5-(2,3-Dihydropyran-2-yl)-3-[(N-methylpyrrolidin-2-yl)methyl]-1-benzoylindole:(39%), from (S)-5-bromo-3-[(N-methylpyrrolidin-2-yl)methyl]-1-benzoylindole (Example 5d); HRMS-FAB+ for $C_{26}H_{28}N_2O_2$; calc. MH+: 401.2229; found MH+:401.2196.

d) (R)-5-(2,3-Dihydropyran-2-yl)-3-[(N-methylpyrrolidin-2-yl)methyl]-1-benzoylindole:(76%), from (R)-5-bromo-3-[(N-methylpyrrolidin-2-yl)methyl]-1-benzoylindole (Example 5e); HRMS-FAB+ for $C_{26}H_{28}N_2O_2$; calc. MH+: 401.2229; found MH+:401.2293.

e) 5-(2,3-Dihydropyran-2-yl)-3-[2-(N,N-dimethylamino)ethyl]-1-benzoylindole: (63%), from 5-bromo-3-[2-(N,N-dimethylamino)ethyl]-1-benzoylindole (Example 5a).

f 3-[2-(-N,N-Dimethylamino)ethyl]-5-(3,4,6-trimethoxyglucal-1-yl)-1-benzoylindole:(70%), from 5-bromo-3-[2-(N,N-dimethylamino)ethyl]1-benzoylindole (Example 5a) and 2-tributylstannyl-tri-O-methoxy-D-glucal (Example 8).

g) 3-(2-Pyrrolidinylethyl)-5-(3,4,6-trimethoxyglucal-1-yl)-1-benzoylindole: (80%), from 5-bromo-3-(2-pyrrolidinylethyl)-1-benzoylindole (Example 5c) and 2-tributylstannyl-tri-O-methoxy-D-glucal (Example 8).

EXAMPLE 19

5-(2,3-Dihydropyran-2-yl)-3-(N-methylpyrrolidin-3-yl)-1H-indole

To a solution of 5-(2,3-dihydropyran-2-yl)-3-(N-methylpyrrolidin-3-yl)-1-benzoylindole (Example 18a, 0.158 g, 0.409 mmol) in methanol (5 mL) was added 2N NaOH (6.8 mmol) and the mixture was heated at reflux for 2 hours. The solution was cooled to room temperature and the solvent was evaporated and the product was extracted with $CH_2Cl_2$ (3×). The organic layer was dried and concentrated by reduced pressure and purified by column chromatography [10% $NH_3$ (2M in MeOH) in $CH_2Cl_2$] to yield the title compound (0.035 g, 30%) as a yellow foam; HRMS-FAB+ for $C_{18}H_{22}N_2O$; calc. MH+:283.1810; found MH+:283.1839.

EXAMPLE 20(a)

5-(2,3-Dihydropyran-2-yl)-3-[2-(N,N-dimethylamino)ethyl]-1H-indole

To 5-(2,3-dihydropyran-2-yl)-3-[2-(N,N-dimethylamino)ethyl]-1-benzoylindole (Example 18e, 0.048, 0.129 mmol) was added a 5% solution of KOH in MeOH (5 mL) followed by methanol (5 mL). The solution was heated at reflux for 3 hours. At this time, the solution was allowed to cool, and was filtered and concentrated by reduced pressure. The crude product was purified by column chromatography [7% $NH_3$ (2M in MeOH) in $CH_2Cl_2$] to yield the title compound as a yellow oil (19.6 mg, 56%); HRMS-FAB+ for $C_{17}H_{22}N_2O$: calc. MH+:271.1810; found MH+:271.1826.

In a like manner, the following additional compounds were prepared:

b) 5-(2,3-Dihydropyran-2-yl)-3-(2-pyrrolidinylethyl)-1H-indole:(74%), from 5-(2,3-dihydropyran-2-yl)-3-(2-pyrrolidinylethyl)-1-benzoylindole (Example 18b); mp 142–148° C.; HRMS-FAB+ for $C_{19}H_{24}N_2O$: calc. MH+:297.1967; found MH+:297.1953.

c) (S)-5-(2,3-Dihydropyran-2-yl)-3-[(N-methylpyrrolidin-2-yl)methyl]-1H-indole: (57%), from (S)-5-(2,3-dihydropyran-2-yl)-3-[(N-methylpyrrolidin-2-yl)methyl]-1-benzoylindole (Example 18c); mp 48–54° C.; HRMS-FAB+ for $C_{19}H_{24}N_2O$: calc. MH+:297.1967; found MH+:297.1979.

d) (R)-5-(2,3-Dihydropyran-2-yl)-3-[(N-methylpyrrolidin-2-yl)methyl]-1H-indole: (25%), from (R)-5-(2,3-dihydropyran-2-yl)-3-[(N-methylpyrrolidin-2-yl)methyl]-1-benzoylindole (Example 18d); HRMS-FAB+ for $C_{19}H_{24}N_2O$: calc. MH+:297.1967; found MH+:297.1989.

e) 3-(2-Pyrrolidinylethyl)- 5-(3,4,6-trimethoxyglucal-1-yl)-1H-indole:(52%), from 3-(2-pyrrolidinylethyl)- 5-(3,4, 6-trimethoxyglucal-1-yl)-1-benzoylindole (Example 18g);

HRMS-FAB$^+$ for $C_{23}H_{32}N_2O_4$: calc. MH$^+$:401.2440; found MH$^+$:401.2475.

f) 3-[2-(N,N-Dimethylamino)ethyl]-5-(3,4,6-trimethoxyglucal-1-yl)-1H-indole: (42%), from 3-[2-(N,N-dimethylamino)ethyl]-5-(3,4,6-trimethoxyglucal-1-yl)-1-benzoylindole (Example 18f); HRMS-FAB$^+$ for $C_{21}H_{30}N_2O_4$: calc MH$^+$: 375.2284; found MH$^+$:375.2292.

EXAMPLE 21

3-(2-Pyrrolidinylethyl)-5-(tetrahydropyran-2-yl)-1H-indole

To a solution of 5-(2,3-dihydropyran-2-yl)-3-(2-pyrrolidinylethyl)-1H-indole (Example 20b, 0.049 g, 0.165 mmol) in absolute ethanol (5 mL) was added NaBH$_3$CN (0.496 mmol) and methanolic HCl [prepared from acetyl chloride (2 mL) and methanol (10 mL)] alternately. The mixture was allowed to stir for 3 hours at which time the reaction was quenched with sodium bicarbonate (sat.) and the product was extracted three times with CH$_2$Cl$_2$. The organic layer was dried (NaSO$_4$), filtered and concentrated. The crude product was purified by column chromatography (7% NH$_3$ in CH$_2$Cl$_2$) to yield the title compound 0.029 g, 59%) as a clear oil; HRMS-FAB$^+$ for $C_{19}H_{26}N_2O$: calc. MH$^+$: 99.2123; found MH$^+$:299.2159.

EXAMPLE 22

General Procedure for Salt Formation

Hydrochloric acid:acid (4 mol. equiv., 1 M in diethyl ether) was added to a solution of the substrate (1 mol. equiv.) in dichloromethane (approx. 0.1 M solution) and the mixture stirred for 20 min. The solvent and excess acid were removed in vacuo and the crude product recrystallized from methanol-ether.

Other salts: The appropriate acid (2 mol. equiv. solid acids) was added to a solution of the substrate (1 mol. equiv.) in methanol (0.14 M solution) and the mixture stirred overnight. The solvent was removed in vacuo and the crude product purified as indicated.

Using the above procedure, the following compounds were prepared:

(a) 5-(1-Aza-1-methylcyclohex-4-yl)-3-[2-(N,N-dimethylamino)ethyl]-1H-indole bishydrochloride from 5-(1-aza-1-methylcyclohex-4-yl)-3-[2-(N,N-dimethylamino)ethyl]-1H-indole (Example 17j); mp 210–213° C.; elemental analysis calculated for $C_{18}H_{29}N_3Cl_2$(1.33H$_2$O before drying): % C 60.33, % H 8.16, % N 11.73, % Cl 19.79; found % C 59.93, % H 8.43, % N 11.43, % Cl 18.82.

(b) 5-(1-Aza-1-methylcyclohex-3-en-4-yl)-3-[2-(N,N-dimethylamino)ethyl]-1H-indole bishydrochloride:(99%) from 5-(1-Aza-1-methylcyclohex-3-en-4-yl)-3-[2-(N,N-dimethylamino)ethyl]-1H-indole (Example 16); mp 278–280° C.; elemental analysis calculated for $C_{18}H_{27}N_3Cl_2$: % C 60.67, % H 7.64, % N 11.79, % Cl 19.90; found % C 60.61, % H 7.30, % N 11.54, % Cl 19.52.

(c) 5-(1-Aza-1-methylcyclohex-3-en-4-yl)-3-[2-(N,N-dimethylamino)ethyl]-1H-indole bissuccinate:(79%, not recrystallized, hygroscopic) from 5-(1-1-aza-1-methylcyclohex-3-en-4-yl)-3-[2 (N,N-dimethylamino) ethyl]-1H-indole (Example 16); elemental analysis calculated for $C_{26}H_{37}N_3O_8$: % C60.10, % H 7.18, % N 8.09; found % C 59.09, % H 6.95, % N 7.51.

(d) 5-(1-Aza-1-methylcyclohex-3-en-4-yl)-3-[2-(N,N-dimethylamino)ethyl]-1H-indole bisoxalate:(86%, crystallized from reaction mixture) from 5-(1aza-1-methylcyclohex-3-en-4-yl)-3-[2-(N,N-dimethylamino) ethyl]-1H-indole (Example 16); mp 194–197° C. (gas evolution accompanied melting); elemental analysis calculated for $C_{22}H_{29}N_3O_8$: % C 57.01, % H 6.31, % N 9.07; found % C 56.35, % H 6.31, % N 8.73.

(e) 5-(1-Aza-1-methylcyclohex-3-en-4-yl)-3-[2-(N,N-dimethylamino)ethyl]-1H-indole bisbenzoate:(39%, recrystallized from methanol and diethyl ether) from 5-(1-aza-1-methylcyclohex-3-en-4-yl)-3-[2-(N,N-dimethylamino) ethyl]-1H-indole (Example 16); mp 105–108° C.; elemental analysis calculated for $C_{32}H_{37}N_3O_4$: % C 72.84, % H 7.07, % N 7.96; found % C 72.69, % H 7.04, % N 7.94.

(f) 5-(1-Aza-1-methylcyclohex-3-en-4-yl)-3-[2-(N,N-dimethylamino)ethyl]-1H-indole bisfumarate:(63%, recrystallized from methanol and diethyl ether) from 5-(1-aza-1-methylcyclohex-3-en-4-yl)-3-[2-(N,N-dimethylamino) ethyl]-1H-indole (Example 16); mp 115–119° C.; elemental analysis calculated for $C_{26}H_{33}N_3O_8$: % C 60–57, % H 6.45, % N 8.15; found % C 61.88, % H 6.70, % N 8.73.

EXAMPLE 23

5-(1Aza-1-methyl4-hydroxycyclohex-4-yl)-3-(1,2,3,6-tetrahydro-1-methyl4-pyridinyl)-1H-indole 5-Bromoindole (4.31 g, 22 mmol), 1-methyl4-piperidone (2.46 mL, 20 mmol) and pyrrolidine (17 mL, 200 mmol) were mixed in ethanol (30 mL) and refluxed for 72 hours. The mixture was cooled to room temperature and the resulting solid, collected by filtration, washed with methanol and dried to provide as 5-bromo-3-(1,2,3,6-tetrahydro-1-methyl4-pyridinyl)-1H-indole white solid (4.40 g, 76%). mp>230° C. dec.

The title compound was prepared by reacting 5-bromo-3-(1,2,3,6-tetrahydro-1-methyl-4-pyridinyl)-1H-indole with 1-methyl4-piperidone using the method described in Example 13.

Summary of Exemplified Compounds of Formulae I and V

| Compound | Ex. # | Compound Name |
|---|---|---|
| | 9a | 5-(Cyclohex-1-en-1-yl)-3-[2-(N,N-dimethylamino)ethyl]-1H-indole |
| | 18a | 5-(2,3-Dihydropyran-2-yl)-3-(N-methylpyrrolidin-3-yl)-1-benzoylindole |
| | 9b | 3-[2-(N,N-Dimethylamino)ethyl]-5-(tetrahydropyran-2-yl)-1H-indole |
| | 19 | 5-(2,3-Dihydropyran-2-yl)-3-(N-methylpyrrolidin-3-yl)-1H-indole |
| | 18c | (S)-5-(2,3-Dihydropyran-2-yl)-3-[(N-methylpyrrolidin-2-yl)methyl]-1-benzoylindole |
| | 20c | (S)-5-(2,3-Dihydropyran-2-yl)-3-[(N-methylpyrrolidin-2-yl)methyl]-1H-indole |

Summary of Exemplified Compounds of Formulae I and V

| Compound | Ex. # | Compound Name |
|---|---|---|
| | 10 | (S)-5-(1-Aza-1-tert-butoxycarbonylcyclohex-3-en-4-yl)-3-[(N-methylpyrrolidin-2-yl)methyl]-1H-indole |
| | 17d | (S)-5-(1-Aza-1-tert-butoxycarbonylcyclohex-4-yl)-3-[(N-methylpyrrolidin-2-yl)methyl]-1H-indole |
| | 20d | (R)-5-(2,3-Dihydropyran-2-yl)-3-[(N-methylpyrrolidin-2-yl)methyl]-1H-indole |
| | 18d | (R)-5-(2,3-Dihydropyran-2-yl)-3-[(N-methylpyrrolidin-2-yl)methyl]-1-benzoylindole |
| | 11 | 5-(1-Aza-1-tert-butoxycarbonylcyclohex-3-en-4-yl)-3-[2-(N,N-dimethylamino)ethyl]-1H-indole |
| | 17e | 5-(1-Aza-1-tert-butoxycarbonylcyclohex-4-yl)-3-[2-(N,N-dimethylamino)ethyl]-1H-indole |

Summary of Exemplified Compounds of Formulae I and V

| Compound | Ex. # | Compound Name |
|---|---|---|
| | 17a | 5-Cyclohexyl-3-[2-(N,N-dimethylamino)ethyl]-1H-indole |
| | 16 | 5-(1-Aza-1-methylcyclohex-3-en-4-yl)-3-[2-(N,N-dimethylamino)ethyl]-1H-indole |
| | 20a | 5-(2,3-Dihydropyran-2-yl)-3-[2-(N,N-dimethylamino)ethyl]-1H-indole |
| | 20b | 5-(2,3-Dihydropyran-2-yl)-3-(2-pyrrolidinylethyl)-1H-indole |
| | 21 | 3-(2-Pyrrolidinylethyl)-5-(tetrahydropyran-2-yl)-1H-indole |

-continued

Summary of Exemplified Compounds of Formulae I and V

| Compound | Ex. # | Compound Name |
|---|---|---|
| | 20e | 3-(2-Pyrrolidinylethyl)-5-(3,4,6-trimethoxyglucal-1-yl)-1H-indole |
| | 12 | 5-(3,4-Dihydropyran-4-yl)-3-[2-(N,N-dimethylamino)ethyl]-1H-indole |
| | 17f | 3-[2-(N,N-Dimethylamino)ethyl]-5-(tetrahydropyran-4-yl)-1H-indole |
| | 13a | 5-(1-Hydroxycyclohex-1-yl)-3-(2-pyrrolidinylethyl)-1H-indole |
| | 14a | 5-(Cyclohex-1-en-1-yl)-3-(2-pyrrolidinylethyl)-1H-indole |

Summary of Exemplified Compounds of Formulae I and V

| Compound | Ex. # | Compound Name |
|---|---|---|
| | 17b | 5-Cyclohexyl-3-(2-pyrrolidinylethyl)-1H-indole |
| | 13b | 5-(1-Aza-1-benzyl-4-hydroxycyclohex-4-yl)-3-(2-pyrrolidinylethyl)-1H-indole |
| | 13c | 5-(1-Aza-1-tert-butoxycarbonyl-4-hydroxycyclohex-4-yl)-3-(2-pyrrolidinylethyl)-1H-indole |
| | 14b and 15a | 5-(1-Aza-1-benzylcyclohex-3-en-4-yl)-3-(2-pyrrolidinylethyl)-1H-indole |
| | 13d | 5-(1-Aza-1-methyl-4-hydroxycyclohex-4-yl)-3-(2-pyrrolidinylethyl)-1H-indole |

-continued

Summary of Exemplified Compounds of Formulae I and V

| Compound | Ex. # | Compound Name |
|---|---|---|
| | 20f | 3-[2-(N,N-Dimethylamino)ethyl]-5-(3,4,6-trimethoxyglucal-1-yl)-1H-indole |
| | 17c | 5-(1-Aza-1-benzylcyclohex-4-yl)-3-(2-pyrrolidinylethyl)-1H-indole |
| | 17g | 5-(1-azacyclohex-4-yl)-3-(2-pyrrolidinylethyl)-1H-indole |
| | 13e | 5-(1-Aza-1-methyl-4-hydroxycyclohex-4-yl)-3-[2-(N,N-dimethylamino)ethyl]-1H-indole |
| | 14c | 5-(1-Aza-4-methylcyclohex-3-en-4-yl)-3-(2-pyrrolidinylethyl)-1H-indole |

Summary of Exemplified Compounds of Formulae I and V

| Compound | Ex. # | Compound Name |
|---|---|---|
| | 18b | 5-(2,3-Dihydropyran-2-yl)-3-(2-pyrrolidinylethyl)-1-benzoylindole |
| | 18e | 5-(2,3-Dihydropyran-2-yl)-3-[2-(N,N-dimethylamino)ethyl]-1-benzoylindole |
| | 18f | 3-[2-(-N,N-Dimethylamino)ethyl]-5-(3,4,6-trimethoxyglucal-1-yl)-1-benzoylindole |
| | 18g | 3-(2-Pyrrolidinylethyl)-5-(3,4,6-trimethoxyglucal-1-yl)-1-benzoylindole |
| | 13f | 3-[2-(N,N-Dimethylamino)ethyl]-5-(4-hydroxytetrahydropyran-4-yl)-1H-indole |

-continued

Summary of Exemplified Compounds of Formulae I and V

| Compound | Ex. # | Compound Name |
|---|---|---|
| | 13g | 5-(4-Hydroxytetrahydropyran-4-yl)-3-(2-pyrrolidinylethyl)-1H-indole |
| | 13h | 3-[2-(N,N-Dimethylamino)ethyl]-5-(4-hydroxythiapyran-4-yl)-1H-indole |
| | 13i | 5-(4-Hydroxythiapyran-4-yl)-3-(2-pyrrolidinylethyl)-1H-indole |
| | 15b | 5-(3,4-dihydropyran-4-yl)-3-(2-pyrrolidinylethyl)-1H-indole |
| | 15c | 3-(2-Pyrrolidinylethyl)-5-(3,4-dihydrothiapyran-4-yl)-1H-indole |
| | 15d | 3-[2-(N,N-Dimethylamino)ethyl]-5-(3,4-dihydrothiapyran-4-yl)-1H-indole |
| | 17h | 5-(tetrahydropyran-4-yl)-3-(2-pyrrolidinylethyl)-1H-indole |

-continued

Summary of Exemplified Compounds of Formulae I and V

| Compound | Ex. # | Compound Name |
|---|---|---|
| (structure) | 17i | 3-[2-(N,N-Dimethylamino)ethyl]-5-(1-thiacyclohex-4-yl)-1H-indole |
| (structure) | 17j | 5-(1-Aza-1-methylcyclohex-4-yl)-3-[2-(N,N-dimethylamino)ethyl]-1H-indole |
| (structure) | 23 | 5-(1-Aza-1-methyl-4-hydroxycyclohex-4-yl)-3-(1,2,3,6-tetrahydro-1-methyl-4-pyridinyl)-1H-indole |

EXAMPLE 24

Agonist Assay

The in vitro evaluation of the 5-$HT_{1D}$-like receptor agonist activity of compounds of the invention was carried out by testing the extent to which they mimic sumatriptan, the marketed antimigraine drug, in contracting the rabbit saphenous vein (Perez, M. et al. J. Med. Chem. 1995, 38:3602–3607).

Tissues were obtained from male New Zealand White rabbits (~3–4 kg) which were sacrificed by an overdose of pentobarbital. The saphenous veins from both the left and right side were cleaned of fat and connective tissue and placed in Krebs solution (118 mM NaCl, 11 mM glucose, 25 mM $NaHCO_3$, 4.7 mM KCl, 2.5 mM $CaCl_2 2H_2O$, 1.2 mM $KH_2PO_4$, and 1.2 mM $MgSO_4 7H_2O$. Ring segments of the vein (4–5 mm in length) were cut and the endothelium gently removed. The segments were mounted in 10 mL baths containing Krebs buffer and were constantly aerated with 95% oxygen/5% carbon dioxide and maintained at 37° C. and pH 7.4 in order to record the isometric tension. A resting tension of 2.5 g was applied and the tissues allowed to equilibrate for 90 minutes, with washing every 15–20 minutes. After the equilibrium period, the rings were depolarized by the addition of two aliquots of KCl (80 mM final concentration) separated by a 20 minute washing period. The tissues were then exposed to prazosin, idazoxan and indomethacin (all 1 μM final concentration) for 30 minutes in order to exclude the actions of $\alpha_1$- and $\alpha_2$-adrenergic receptors and prostaglandin receptors respectively. Cumulative concentration-effect curves were then constructed for sumatriptan and the test compounds. Responses were calculated as a percentage of the maximal contraction evoked by 80 mM KCl. Only one compound was tested per preparation.

The following Table illustrates the in vitro activities for the compounds of the invention on the rabbit isolated saphenous vein. $EC_{50}$ represents the concentration of the compound which causes 50% of the maximum contraction effected by it.

| Compound/Example # | $EC_{50}$ (μM) |
|---|---|
| sumatriptan | 0.22 |
| 9b | 0.16 |
| 9a | 0.96 |
| 15 | 0.22 |
| 17a | 0.25 |
| 20c | 1.7 |
| 17d | 0.75 |
| 16 | 0.75 |

EXAMPLE 25

Inhibitition of Protein Extravasation

Compounds of the inventions were evaluated for their ability to block neurogenic inflammation via inhibition of protein extravasation using the trigeminal stimulation assay as described in Markowitz, et al. J. Neurosci. 1987, 7:4129 and Lee, et al. Brain Res, 1993, 626:303. This is believed to indicate a compound's ability to act as an agonist at the 5-$HT_{1D\alpha}$ and/or 5-$HT_{1F}$ receptors.

Guinea pigs were anesthetized with pentobarbitone sodium (60 mg $kg^{-1}$, i.p.). Animals were placed in a stereotaxic frame (DKI 900, David Kopf Instruments, Tujunga, Calif., U.S.A.). The right femoral vein was exposed and [$^{125}$I]-BSA (50 μCi $kg^{-1}$) was injected as a bolus. With the incisor bar set at −1.5 mm from the horizontal line, the calvarium was exposed by a midline incision. Symmetrical burr holes (2 mm in diameter) were drilled at 3.7 mm posterior to the bregma and 3.2 mm lateral to the sagittal suture. Bipolar electrodes (50 mm shaft, Rhodes Medical Instruments, Woodland Hills, Calif., U.S.A.) were lowered into the trigeminal ganglia to a depth of 9.5 mm from the dura mater overlying the dorsal surface of the brain. The right trigeminal ganglion was stimulated for 5 min (0.6 mA, 5 ms, 5 Hz) (Pulsemaster A300 and Stimulus Isolator A365, World Precision Instruments, San Carlos, Calif., U.S.A.; Oscilloscope V-134, Hitachi Densi, Tokyo, Japan). In order to remove iodinated albumin completely from the lumen of blood vessels, animals were perfused via the left cardiac ventricle for 2 min with saline at a constant pressure of 100 mm Hg. After opening the skull, the brain was removed. The dura mater was rinsed and dissected bilaterally. Radioactivity was determined on two sides with a gamma counter (Micromedic 4/600, Micromedic Systems, Inc., Huntsville, Ala., U.S.A.) as previously described (Markowitz, et al., 1987 and Lee, et al., 1993).

Results from this assay, expressed as an $ID_{50}$ (nM/kg of drug), are shown in the table below for the reference compound, sumatriptan, and the compound of example 16.

| Compound/Example # | $ID_{50}$ (nM/kg) |
|---|---|
| sumatriptan | 3.3–7 |
| 16 | 1.03 ± 1.45 |

EXAMPLE 26

Pharmaceutical Examples

Tablets

These may be prepared by the normal methods such as wet granulation or direct compression.

| A. Direct Compression | mg/tablet |
|---|---|
| Active ingredient | 10.0 |
| Microcrystalline Cellulose USP | 188.5 |
| Magnesium Stearate BP | 1.5 |
| Compression weight | 200.0 |

The active ingredient is sieved through a suitable sieve, blended with the excipients and compressed using 7 mm diameter punches. Tablets of other strengths may be prepared by altering the compression weight and using punches to suit.

| B. Wet Granulation | mg/tablet |
|---|---|
| Active ingredient | 10.0 |
| Lactose BP | 143.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

| C. For Buccal Administration | mg/tablet |
|---|---|
| Active ingredient | 10.0 |
| Lactose BP | 86.8 |
| Sucrose BP | 86.7 |
| Hydroxypropyl methylcellulose | 15.0 |
| Magnesium Stearate BP | 1.5 |
| Compression weight | 200.0 |

The active ingredient is sieved through a suitable sieve and blended with the lactose, sucrose and hydroxypropylmethylcellulose. Suitable volumes of purified water are added and the powders are granulated. After drying, the granules are screened and blended with the magnesium stearate. The granules are then compressed into tablets using suitable punches.

The tablets may be film-coated with suitable film-forming materials, such as hydroxypropyl methylcellulose, using standard techniques. Alternatively the tablets may be sugar coated.

| Capsules | mg/capsule |
|---|---|
| Active ingredient | 10.0 |
| *Starch 1500 | 89.0 |
| Magnesium Stearate BP | 1.0 |
| Fill Weight | 100.0 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| Syrup | mg/5 ml dose |
|---|---|
| Active ingredient | 10.0 |
| Sucrose BP | 2750.0 |
| Glycerine BP | 500.0 |
| Buffer | as required |
| Flavour | as required |
| Colour | as required |
| Preservative | as required |
| Distilled water to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup produced is clarified by filtration.

| Suppositories | |
|---|---|
| Active ingredient | 10.0 mg |
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

| Injection for Intravenous Administration | % w/v |
|---|---|
| Active ingredient | 0.2 |
| Sodium Chloride BP | as required |
| Water for Injection BP to | 100.00 |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

| Inhalation Cartridges | mg/cartridge |
|---|---|
| Active ingredient micronised | 1.0 |
| Lactose BP | 39.0 |

The active ingredient is micronised (Microniser is a Registered Trade Mark) in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler (Registered Trade Mark).

| Metered Dose Pressurised Aerosol | mg/metered dose | per can |
|---|---|---|
| Active ingredient micronised | 0.500 | 120.0 mg |
| Oleic Acid BP | 0.050 | 12.0 mg |
| Trichlorofluoromethane BP | 22.250 | 5.34 mg |
| Dichlorodifluoromethane BP | 62.2 | 14.92 g |

The active ingredient is micronised in a fluid energy mill to a fine particle size range. The oleic acid is mixed with the trichlorofluoromethane at a temperature of 10–15° C. and the pulverized drug is mixed into the solution with a high shear mixer. The suspension is metered into aluminum aerosol cans and suitable metering valves, delivering a metered amount of 85 mg of suspension, are crimped onto the cans and the dichlorodifluoromethane is pressure filled into the cans through the valves.

We claim:

1. A compound according to Formula I:

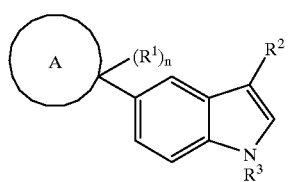

I wherein A is an optionally substituted, six-membered, non-aromatic heterocycle having one O, S or N ring heteroatom, wherein the S ring heteroatom is unoxidized or optionally oxidized to form SO or $SO_2$, wherein the N ring heteroatom has $R^4$ directly attached;

$R^1$ is selected from H and OH;

n is 0 or 1 as permitted by chemical structure;

$R^2$ is selected from $CR^5R^6CH_2NR^7R^8$ or a group of formula II, III or IV:

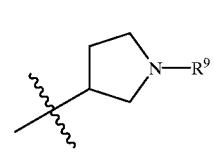

II

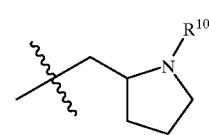

III

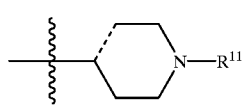

IV $R^3$ is selected from H and benzoyl;

$R^4$ is selected from H, loweralkyl, benzyl, loweralkylcarbonyl, butoxycarbonyl, loweralkylaminocarbonyl, loweralkylaminothiocarbonyl, loweralkylaminoimido and loweralkoxy-substituted loweralkyl;

$R^5$ and $R^6$ are independently selected from H, loweralkoxy and hydroxy;

$R^7$ and $R^8$ are independently selected from H and loweralkyl or $R^7$ and $R^8$ form an alkylene bridge which, together with the nitrogen atom to which they are attached, creates an optionally substituted 3- to 6-membered ring;

denotes a single or double bond; and $R^9$, $R^{10}$ and $R^{11}$ are independently selected from H and loweralkyl.

2. A compound according to claim 1, wherein A is an unsubstituted six-membered heterocycle having one ring heteroatom selected from O, S or N, wherein the S ring heteroatom is unoxidized or optionally oxidized to form SO or $SO_2$, wherein the N ring heteroatom has $R^4$ directly attached.

3. A compound according to claim 2, wherein A is an unsubstituted six-membered heterocycle having one ring heteroatom selected from O, S and N, wherein the N ring heteroatom has $R^4$ directly attached.

4. A compound according to claim 1, wherein A is a six-membered, non-aromatic, optionally substituted heterocycle selected from dihydropyran, tetrahydropyran, dihydrothiapyran, tetrahydrothiapyran, azacyclohexane and azacyclohexene.

5. A compound according to claim 4, wherein A is a six-membered, non-aromatic heterocycle selected from 1-$R^4$-azacyclohexan-4-yl; 1-$R^4$-azacyclohex-3-en-4-yl; tetrahydrothiapyran-4-yl; 3,4-dihydrothiapyran-4-yl; 2,3-dihydropyran-2-yl; tetrahydropyran-2-yl; 3,4-dihydropyran-4-yl; and tetrahydropyran-4-yl.

6. A compound according to claim 5, wherein A is selected from 1-$R^4$-azacyclohex-3-en-4-yl and 1-$R^4$-azacyclohexan-4yl.

7. A compound according to claim 6, wherein $R^4$ is loweralkyl.

8. A compound according to claim 7, wherein A is 1-$R^4$-azacyclohex-3-en-4-yl and $R^4$ is methyl.

9. A compound according to claim 7, wherein A is 1-$R^4$-azacyclohexan-4-yl and $R^4$ is methyl.

10. A compound according to claim 1, wherein $R^3$ is H.

11. A compound according to claim 10, wherein $R^2$ is $CR^5R^6CH_2NR^7R^8$ and one of $R^5$ and $R^6$ is selected from loweralkoxy or hydroxy and the other is H.

12. A compound according to claim 11, wherein $R^5$ and $R^6$ are both H.

13. A compound according to claim 12, wherein $R^7$ and $R^8$ are both loweralkyl.

14. A compound according to claim 13, wherein $R^7$ and $R^8$ are both methyl.

15. A compound according to claim 12, wherein $R^7$ and $R^8$ form an alkylene bridge which, together with the nitrogen atom to which they are attached, form an optionally substituted 3- to 6-membered ring.

16. A compound according to claim 15, wherein $R^7$ and $R^8$ form an alkylene bridge which, together with the nitrogen atom to which they are attached, form an optionally substituted 5- or 6-membered ring.

17. A compound according to claim 16, wherein $R^7$ and $R^8$, together with the nitrogen atom to which they are attached, form an unsubstituted pyrrolidine ring.

18. A compound according to claim 10, wherein $R^2$ is a group of formula II.

19. A compound according to claim 18, wherein $R^9$ is methyl.

20. A compound according to claim 10, wherein $R^2$ is a group of formula III.

21. A compound according to claim 20, wherein $R^{10}$ is methyl.

22. A compound according to claim 10, wherein $R^2$ is a group of Formula IV.

23. A compound according to claim 22, wherein $R^{11}$ is methyl.

24. A compound according to claim 1, which is selected from:
   3-[2-(N,N-Dimethylamino)ethyl]-5-(tetrahydropyran-2-yl)-1H-indole;
   (S)-5-(1-Aza-1-tert-butoxycarbonylcyclohex-3-en-4-yl)-3-[(N-methylpyrrolidin-2-yl)methyl]-1H-indole;
   5-(1-Aza-1-tert-butoxycarbonylcyclohex-3-en-4-yl)-3-[2-(N,N-dimethylamino)ethyl]-1H-indole;
   5-(3,4-Dihydropyran-4-yl)-3-[2-(N,N-dimethylamino)ethyl]-1H-indole;
   5-(1-Aza-1-benzyl-4-hydroxycyclohex-4-yl)-3-(2-pyrrolidinylethyl)-1H-indole;
   5-(1-Aza-1-tert-butoxycarbonyl-4-hydroxycyclohex-4-yl)-3-(2-pyrrolidinylethyl)-1H-indole;
   5-(1-Aza-1-methyl-4-hydroxycyclohex-4-yl)-3-(2-pyrrolidinylethyl)-1H-indole;
   5-(1-Aza-1-methyl-4-hydroxycyclohex-4-yl)-3-[2-(N,N-dimethylamino)ethyl]-1H-indole;
   5-(1-Aza-1-benzylcyclohex-3-en-4-yl)-3-(2-pyrrolidinylethyl)-1H-indole;
   5-(1-Aza-1-methylcyclohex-3-en-4-yl)-3-(2-pyrrolidinylethyl)-1H-indole;
   5-(1-Aza-1-methylcyclohex-3-en-4-yl)-3-[2-(N,N-dimethylamino)ethy]-1H-indole;
   5-(1-Aza-1-benzylcyclohex-4-yl)-3-(2-pyrrolidinylethyl)-1H-indole;
   -5-(1-Aza-1-tert-butoxycarbonylcyclohex-4-yl)-3-[(N-methylpyrrolidin-2-yl)methyl]-1H-indole;
   5-(1-Aza-1-tert-butoxycarbonylcyclohex-4-yl)-3-[2-(N,N-dimethylamino)ethyl]-1H-indole;
   3-[2-(N,N-Dimethylamino)ethyl]-5-(tetrahydropyran-4-yl)-1H-indole;
   5-(1-Azacyclohex-4-yl)-3-(2-pyrrolidinylethyl)-1H-indole;
   5-(2,3-Dihydropyran-2-yl)-3-(N-methylpyrrolidin-3-yl)-1-benzoylindole;
   5-(2,3-Dihydropyran-2-yl)-3-(2-pyrrolidinylethyl)-1-benzoylindole;
   (S)-5-(2,3-Dihydropyran-2-yl)-3-[(N-methylpyrrolidin-2-yl)methyl]-1-benzoylindole;
   (R)-5-(2,3-Dihydropyran-2-yl)-3-[(N-methylpyrrolidin-2-yl)methyl]-1-benzoylindole;
   5-(2,3-Dihydropyran-2-yl)-3-[2-(N,N-dimethylamino)ethyl]-1-benzoylindole;
   3-[2-(N,N-Dimethylamino)ethyl]-5-(3,4,6-trimethoxyglucal-1-yl)-1-benzoylindole;
   3-(2-Pyrrolidinylethyl)-5-(3,4,6-trimethoxyglucal-1-yl)-1-benzoylindole;
   5-(2,3-Dihydropyran-2-yl)-3-(N-methylpyrrolidin-3-yl)-1H-indole;
   5-(2,3-Dihydropyran-2-yl)-3-[2-(N,N-dimethylamino)ethyl]-1H-indole;
   5-(2,3-Dihydropyran-2-yl)-3-(2-pyrrolidinylethyl)-1H-indole;
   (S)-5-(2,3-Dihydropyran-2-yl)-3-[(N-methylpyrrolidin-2-yl)methyl]-1H-indole;
   (R)-5-(2,3-Dihydropyran-2-yl)-3-[(N-methylpyrrolidin-2-yl)methyl]-1H-indole;
   3-(2-Pyrrolidinylethyl)-5-(3,4,6-trimethoxyglucal-1-yl)-1H-indole;
   3-[2-(N,N-Dimethylamino)ethyl]-5-(3,4,6-trimethoxyglucal-1-yl)-1H-indole;
   3-(2-Pyrrolidinylethyl)-5-(tetrahydropyran-2-yl)-1H-indole;
   5-(2,3-Dihydropyran-2-yl)-3-(2-pyrrolidinylethyl)-1-benzoylindole;
   5-(2,3-Dihydropyran-2-yl)-3-[2-(N,N-dimethylamino)ethyl]-1-benzoylindole;
   3-[2-(-N,N-Dimethylamino)ethyl]-5-(3,4,6-trimethoxyglucal-1-yl)-1-benzoylindole;
   3-(2-Pyrrolidinylethyl)-5-(3,4,6-trimethoxyglucal-1-yl)-1-benzoylindole;
   3-[2-(N,N-Dimethylamino)ethyl]-5-(4-hydroxytetrahydropyran-4-yl)-1H-indole;
   5-(4-Hydroxytetrahydropyran-4-yl)-3-(2-pyrrolidinylethyl)-1H-indole;
   3-[2-(N,N-Dimethylamino)ethyl]-5-(4-hydroxythiapyran-4-yl)-1H-indole;
   5-(4-Hydroxythiapyran-4-yl)-3-(2-pyrrolidinylethyl)-1H-indole;
   5-(3,4-Dihydropyran-4-yl)-3-(2-pyrrolidinylethyl)-1H-indole;
   3-(2-Pyrrolidinylethyl)-5-(3,4-dihydrothiapyran-4-yl-1H-indole;
   3-[2-(N,N-Dimethylamino)ethyl]-5-(3,4-dihydrothiapyran-4-yl)-1H-indole;
   3-(2-Pyrrolidinylethyl)-5-(tetrahydropyran-4-yl)-1H-indole;

3-[2-(N,N-Dimethylamino)ethyl]-5-(1-thiacyclohex-4-yl)-1H-indole;

3-[2-(N,N-Dimethylamino)ethyl]-5-(4-hydroxytetrahydropyran-4-yl)-1H-indole;

5-(1-Aza-1-methyl-4-hydroxycyclohex-4-yl)-3-(1,2,3,6-tetrahydro-1-methyl-4 pyridinyl)-1H-indole; and 5-(1-Aza-1-methylcyclohex-4-yl)-3-[2-(N,N-dimethylamino)ethyl]-1H-indole.

25. A compound according to claim 24, which is selected from:

3-[2-(N,N-Dimethylamino)ethyl]-5-(tetrahydropyran-2-yl)-1H-indole;

(S)-5-(1-Aza-1-tert-butoxycarbonylcyclohex-3-en-4-yl)-3-[(N-methylpyrrolidin-2-yl)methyl]-1H-indole;

5-(1-Aza-1-tert-butoxycarbonylcyclohex-3-en-4-yl)-3-[2-(N,N-dimethylamino)ethyl]-1H-indole;

5-(3,4-Dihydropyran-4-yl)-3-[2-(N,N-dimethylamino)ethyl]-1H-indole;

5-(1-Aza-1-methyl-4-hydroxycyclohex-4-yl)-3-[2-(N,N-dimethylamino)ethyl]-1H-indole;

5-(1-Aza-1-benzylcyclohex-3-en-4-yl)-3-(2-pyrrolidinylethyl)-1H-indole;

5-(1-Aza-1-methylcyclohex-3-en-4-yl)-3-(2-pyrrolidinylethyl)-1H-indole;

5-(1-Aza-1-methylcyclohex-3-en-4-yl)-3-[2-(N,N-dimethylamino)ethyl]-1H-indole;

5-(1-Aza-1-benzylcyclohex-4-yl)-3-(2-pyrrolidinylethyl)-1H-indole;

(S)-5-(1-Aza-1-tert-butoxycarbonylcyclohex-4-yl)-3-[(N-methylpyrrolidin-2-yl)methyl]-1H-indole;

5-(1-Aza-1-tert-butoxycarbonylcyclohex-4-yl)-3-[2-(N,N-dimethylamino)ethyl]-1H-indole;

3-[2-(N,N-Dimethylamino)ethy]-5-(tetrahydropyran-4-yl)-1H-indole;

5-(1-Azacyclohex-4-yl)-3-(2-pyrrolidinylethyl)-1H-indole;

5-(2,3-Dihydropyran-2-yl)-3-(N-methylpyrrolidin-3-yl)-1H-indole;

5-(2,3-Dihydropyran-2-yl)-3-[2-(N,N-dimethylamino)ethyl]-1H-indole;

5-(2,3-Dihydropyran-2-yl)-3-(2-pyrrolidinylethyl)-1H-indole;

(S)-5-(2,3-Dihydropyran-2-yl)-3-[(N-methylpyrrolidin-2-yl)methyl]-1H-indole;

(R)-5-(2,3-Dihydropyran-2-yl)-3-[(N-methylpyrrolidin-2-yl)methyl]-1H-indole;

3-(2-Pyrrolidinylethyl)-5-(tetrahydropyran-2-yl)-1H-indole;

3-[2-(N,N-Dimethylamino)ethyl]-5-(4-hydroxytetrahydropyran-4-yl)-1H-indole;

5-(4-Hydroxytetrahydropyran-4-yl)-3-(2-pyrrolidinylethyl)-1H-indole;

3-[2-(N,N-Dimethylamino)ethyl]-5-(4-hydroxythiapyran-4-yl)-1H-indole;

5-(4-Hydroxythiapyran-4yl)-3-(2-pyrrolidinylethyl)-1H-indole;

5-(3,4-Dihydropyran-4-yl)-3-(2-pyrrolidinylethyl)-1H-indole;

3-(2-Pyrrolidinylethyl)-5-(3,4-dihydrothiapyran-4-yl)-1H-indole;

3-[2-(N,N-Dimethylamino)ethyl]-5-(3,4-dihydrothiapyran-4-yl)-1H-indole;

3-(2-Pyrrolidinylethyl)-5-(tetrahydropyran-4-yl)-1H-indole;

3-[2-(N,N-Dimethylamino)ethyl]-5-(1-thiacyclohex-4-yl)-1H-indole;

3-[2-(N,N-Dimethylamino)ethyl]-5-(4-hydroxytetrahydropyran-4-yl)-1H-indole;

5-(1-Aza-1-methyl-4-hydroxycyclohex-4-yl)-3-(1,2,3,6-tetrahydro-1-methyl-4-pyridinyl)-1H-indole; and 5-(1-Aza-1-methylcyclohex-4-yl)-3-[2-(N,N-dimethylamino)ethyl]-1H-indole.

26. A compound according to claim 25, which is selected from:

5-(1-Aza-1-methyl-4-hydroxycyclohex-4-yl)-3-[2-(N,N-dimethylamino)ethyl]-1H-indole;

5-(1-Aza-1-benzylcyclohex-3-en-4-yl)-3-(2-pyrrolidinylethyl)-1H-indole;

5-(1-Aza-1-methylcyclohex-3-en-4-yl)-3-[2-(N,N-dimethylamino)ethyl]-1H-indole;

5-(1-Aza-1-benzylcyclohex-4-yl)-3-(2-pyrrolidinylethyl)-1H-indole;

5-(1-Aza-1-tert-butoxycarbonylcyclohex-4-yl)-3-[2-(N,N-dimethylamino)ethyl]-1H-indole;

5-(1-Azacyclohex-4-yl)-3-(2-pyrrolidinylethyl)-1H-indole;

5-(2,3-Dihydropyran-2-yl)-3-[2-(N,N-dimethylamino)ethyl]-1H-indole;

5-(2,3-Dihydropyran-2-yl)-3-(2-pyrrolidinylethyl)-1H-indole;

(S)-5-(2,3-Dihydropyran-2-yl)-3-[(N-methylpyrrolidin-2-yl)methyl]-1H-indole;

3-[2-(N,N-Dimethylamino)ethyl]-5-(4-hydroxythiapyran-4-yl)-1H-indole;

5-(4-Hydroxythiapyran-4-yl)-3-(2-pyrrolidinylethyl)-1H-indole;

5-(3,4-Dihydropyran-4-yl)-3-(2-pyrrolidinylethyl)-1H-indole;

3-(2-Pyrrolidinylethyl)-5-(3,4-dihydrothiapyran-4-yl)-1H-indole;

3-[2-(N,N-Dimethylamino)ethyl]-5-(tetrahydropyran-4-yl)-1H-indole;

3-[2-(N,N-Dimethylamino)ethyl]-5-(3,4-dihydrothiapyran-4-yl)-1H-indole;

3-(2-Pyrrolidinylethyl)-5-(tetrahydropyran-4-yl)-1H-indole;

5-(1-Aza-1-methylcyclohex-4-yl)-3-[2-(N,N-dimethylamino)ethyl]-1H-indole; and

3-[2-(N,N-Dimethylamino)ethyl]-5-(4-hydroxytetrahydropyran-4-yl)-1H-indole.

27. A compound according to claim 26, which is selected from:

5-(1-Aza-1-methylcyclohex-3-en-4-yl)-3-[2-(N,N-dimethylamino)ethyl]-1H-indole;

5-(4-Hydroxythiapyran-4yl)-3-(2-pyrrolidinylethyl)-1H-indole;

5-(3,4-Dihydropyran-4-yl)-3-(2-pyrrolidinylethyl)-1H-indole;

3-[2-(N,N-Dimethylamino)ethyl]-5-(tetrahydropyran-4-yl)-1H-indole;

3-[2-(N,N-Dimethylamino)ethyl]-5-(3,4-dihydrothiapyran-4-yl)-1H-indole;

3-(2-Pyrrolidinylethyl)-5-(tetrahydropyran-4-yl)-1H-indole; and 5-(1-Aza-1-methylcyclohex-4-yl)-3-[2-(N,N-dimethylamino)ethyl]-1H-indole.

28. A compound according to claim 27, which is 5-(1-aza-1-methylcyclohex-3-en-4-yl)-3-[2-(N,N-dimethylamino)ethyl]-1H-indole.

29. A compound according to claim 27, which is 5-(1-aza-1-methylcyclohex-4-yl)-3-[2-(N,N-dimethylamino)ethyl]-1H-indole.

30. A compound according to claim 1 wherein A is a six-membered, non-aromatic heterocycle having one ring heteroatom selected from O, S or N, wherein the S ring heteroatom is unoxidized or optionally oxidized to form SO or $SO_2$, wherein the N ring heteroatom has $R^4$ directly attached, wherein the heterocycle is optionally substituted by one, two or three groups selected independently from loweralkyl, hydroxy, loweralkoxy and loweralkoxy-substituted loweralkylene.

31. A compound according to claim 1, wherein A is an optionally substituted six-membered nonaromatic heterocycle having one N ring heteroatom, wherein said N ring heteroatom has $R^4$ directly attached.

32. A compound according to claim 31, wherein $R^4$ is loweralkyl.

33. A compound according to claim 1 in radiolabeled form.

34. A pharmaceutical composition, comprising a pharmaceutically acceptable carrier and, in an amount effective to stimulate a $5\text{-HT}_{1D}$-like receptor, a compound of Formula V:

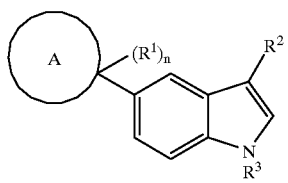

V wherein A is an optionally substituted, six-membered, non-aromatic heterocycle having one O, S or N ring heteroatom, wherein the S ring heteroatom is unoxidized or optionally oxidized to form SO or $SO_2$, wherein the N ring heteroatom has $R^4$ directly attached;

$R^1$ is selected from H and OH;

n is 0 or 1 as permitted by chemical structure;

$R^2$ is selected from $CR^5R^6CH_2NR^7R^8$ or a group of formula II, III or IV:

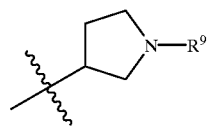

II

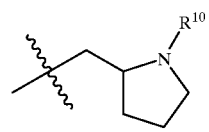

III

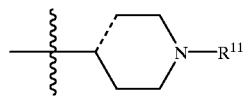

IV $R^3$ is selected from H and benzoyl;

$R^4$ is selected from H, loweralkyl, benzyl, loweralkylcarbonyl, butoxycarbonyl, loweralkylaminocarbonyl, loweralkylaminothiocarbonyl, loweralkylaminoimido and loweralkoxy-substituted loweralkyl;

$R^5$ and $R^6$ are independently selected from H, loweralkoxy and hydroxy;

$R^7$ and $R^8$ are independently selected from H and loweralkyl or $R^7$ and $R^8$ form an alkylene bridge which, together with the nitrogen atom to which they are attached, creates an optionally substituted 3- to 6-membered ring;

denotes a single or double bond; and $R^9$, $R^{10}$ and $R^{11}$ are independently selected from H and loweralkyl.

35. A pharmaceutical composition, comprising a compound of claim 31 in an amount effective in stimulating a $5\text{-HT}_{1D}$-like receptor and a pharmaceutically acceptable carrier.

36. A pharmaceutical composition according to claim 34, wherein said compound is 5-(1-aza-1-methylcyclohex-3-en-4-yl)-3-[2-(N,N-dimethylamino)ethyl]-1H-indole.

37. A pharmaceutical composition according to claim 34, wherein said compound is 5-(1-aza-1-methylcyclohex-4-yl)-3-[2-(N,N-dimethylamino)ethyl]-1H-indole.

38. A method for treating a patient having a medical condition for which a $5\text{-HT}_{1D}$-like receptor agonist is indicated, comprising the step of administering to the patient a pharmaceutical composition as defined in claim 34.

39. A method for treating a patient according to claim 38, wherein the medical condition is migraine.

40. A method for treating a patient having a medical condition for which a $5\text{-HT}_{1D}$-like receptor agonist is indicated, comprising administering a compound of claim 31, in an amount effective in stimulating a $5\text{-HT}_{1D}$-like receptor, to said patient.

* * * * *